United States Patent [19]

Taylor et al.

[11] 4,447,422
[45] May 8, 1984

[54] PENICILLINS AND COMPOSITIONS CONTAINING THEM

[75] Inventors: Andrew W. Taylor, Reigate; Richard G. Adams, Woking, both of England

[73] Assignee: Beecham Group p.l.c., England

[21] Appl. No.: 385,805

[22] Filed: Jun. 7, 1982

[30] Foreign Application Priority Data

Jun. 16, 1981 [GB] United Kingdom ................. 8118552

[51] Int. Cl.³ .................. H01K 31/505; C09D 499/10
[52] U.S. Cl. ................................ 424/229; 260/239.1; 424/251
[58] Field of Search ..................... 260/239.1; 424/229, 424/251

[56] References Cited

U.S. PATENT DOCUMENTS 4,263,302 4/1981 Matsubara et al. .......... 260/239.1 X
4,267,180 5/1981 Haskell et al. ....................... 424/251
4,315,933 2/1982 Mich et al. ........................... 424/251

Primary Examiner—Natalie Trousof
Assistant Examiner—Vera C. Clarke
Attorney, Agent, or Firm—Jacobs & Jacobs

[57] ABSTRACT

A compound of formula (I) or a pharmaceutically acceptable salt or in vivo hydrolysable ester thereof:

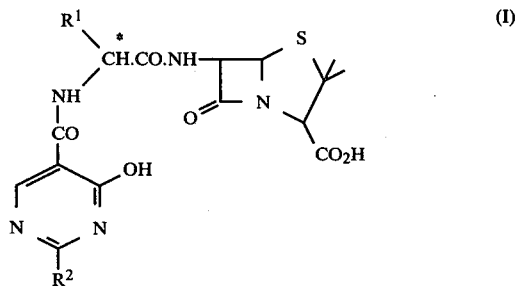

wherein $R^1$ is phenyl, 4-hydroxy phenyl, 3,4-dihydroxyphenyl, 3,4-diacetoxyphenyl or a 5- or 6- membered heterocyclic ring containing up to three heteroatoms selected from oxygen, sulphur or nitrogen, optionally substituted with hydroxy, amino, halogen or $C_{1-6}$ alkoxy; and $R^2$ is a sub-group of formula (A):

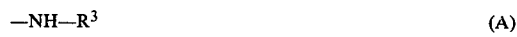

wherein $R^3$ is an optionally substituted $C_{1-10}$ alkyl or $C_{3-7}$ cycloalkyl group; or $R^2$ is a sub-group of formula (B):

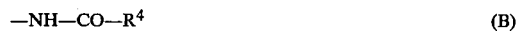

wherein $R^4$ is an aryl group, an optionally substituted $C_{1-10}$ alkyl group or a $C_{1-6}$ alkyloxy group optionally substituted by an aryl group.

21 Claims, No Drawings

PENICILLINS AND COMPOSITIONS CONTAINING THEM

This invention relates to a class of penicillins which have antibacterial activity and are of value in the treatment of infections in animals, including mammals and especially humans. In particular the invention relates to a class of penicillins with the pyrimidino group in the side-chain. The invention also relates to a process for the preparation of such compounds, and to pharmaceutical compositions comprising them.

The present invention provides a compound of formula (I) or a pharmaceutically acceptable salt or in vivo hydrolysable ester thereof:

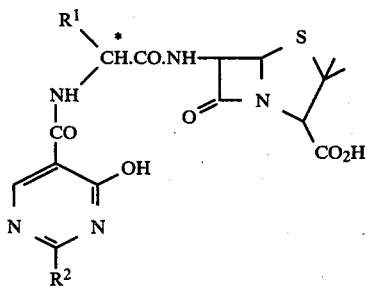

wherein $R^1$ is phenyl, 4-hydroxy phenyl, 3,4-dihydroxyphenyl, 3,4-diacetoxyphenyl or a 5- or 6-membered heterocyclic ring containing up to three heteroatoms selected from oxygen, sulphur or nitrogen, optionally substituted with hydroxy, amino, halogen or $C_{1-6}$ alkoxy; and $R^2$ is a sub-group of formula (A):

$$-NH-R^3 \quad (A)$$

wherein $R^3$ is an optionally substituted $C_{1-10}$ alkyl or $C_{3-7}$ cycloalkyl group; or $R^2$ is a sub-group of formula (B):

$$-NH-CO-R^4 \quad (B)$$

wherein $R^4$ is an aryl group, an optionally substituted $C_{1-10}$ alkyl group or a $C_{1-6}$ alkyloxy group optionally substituted by an aryl group.

The compounds of the present invention include the pharmaceutically acceptable esters of compound (I) which hydrolyse readily in the human body to produce the parent acid, for example acyloxyalkyl groups such as acetoxymethyl, pivaloyloxymethyl, α-acetoxyethyl, α-acetoxyethyl and α-pivaloyloxyethyl groups; alkoxycarbonyloxyalkyl groups, such as ethoxycarbonyloxymethyl and α-ethoxycarbonyloxyethyl; dialkylaminoalkyl groups such as dimethylaminomethyl, dimethylaminoethyl, diethylaminomethyl or diethylaminoethyl; and lactone groups such as phthalidyl or dimethoxyphthalidyl.

The compounds of the present invention also include the pharmaceutically acceptable esters of compound (I) which hydrolyse readily in the human body to produce the hydroxyl group of the pyrimidino group, for example the formyl ester.

Suitable salts of the compound of formula (I) include metal salts e.g. aluminium, alkali metal salts such as sodium or potassium alkaline earth metal salts such as calcium or magnesium and ammonium or substituted ammonium salts, for example those with lower alkylamines such as triethylamine, hydroxy-lower alkylamines such as 2-hydroxyethylamine, bis-(2-hydroxyethyl)-amine or tri-(2-hydroxyethyl)-amine, cycloalkylamines such as bicyclohexylamine, or with procaine, dibenzylamine, N,N-dibenzylethylenediamine, 1-ephenamine, N-ethylpiperidine, N-benzyl-β-phenethylamine, dehydroabietylamine, N,N'-bisdehydroabietylamineethylenediamine, or bases of the pyridine type such as pyridine, collidine or quinoline, or other amines which have been used to form salts with known penicillins.

The carbon atom marked * in formula (I) is asymmetric so that the compounds may exist as two optically active diastereoisomers. In general that prepared from the D-side chain exhibits the highest antibacterial activity.

In formula (I), the group $R^1$ is preferably phenyl, 4-hydroxyphenyl, 3,4-dihydroxyphenyl, 2-thienyl, 3-thienyl or 2-amino-4-thiazolyl.

Suitable groups $R^3$ and $R^4$ include $C_{1-6}$ alkyl optionally substituted with up to three halogen, carboxy, $C_{1-6}$ alkoxycarbonyl, carbamoyl, aryl, heterocyclyl, hydroxy, $C_{1-6}$ alkanoyloxy, amino, mono- and di-($C_{1-6}$) alkylamino, aryl, amino, $C_{1-6}$ alkylthio, $C_{1-6}$ alkyloxy, $C_{3-7}$ cycloalkyl or vinyl groups.

When used herein the term "aryl" includes phenyl and naphthyl optionally substituted with up to five halogen, $C_{1-6}$ alkyl, $C_{1-6}$ alkoxy, halo ($C_{1-6}$) alkyl, hydroxy, amino, sulphonamido, carboxy, $C_{1-6}$ alkoxycarbonyl, or $C_{1-6}$ alkoxycarbonyl-($C_{1-6}$)-alkyl groups.

The term "heterocyclyl" includes single or fused rings comprising up to four hetero atoms in the ring selected from oxygen, nitrogen and sulphur and optionally substituted with up to three halogen, $C_{1-6}$ alkyl, $C_{1-6}$ alkoxy, halo-($C_{1-6}$)-alkyl, hydroxy, amino, carboxy, $C_{1-6}$ alkoxycarbonyl, $C_{1-6}$ alkoxycarbonyl($C_{1-6}$)alkyl, aryl or oxo groups.

Suitable $C_{1-10}$ alkyl groups for $R^3$ and $R^4$ may be straight or branched chain and include ethyl n- or iso-propyl, n-, sec-, iso- or tert-butyl, and hexyl. In those cases where the $C_{1-10}$ alkyl group carries a substituent the preferred $C_{1-10}$ alkyl groups for $R^3$ and $R^4$ include methyl, ethyl and n-propyl. In those cases where the $C_{1-10}$ alkyl group is unsubstituted the preferred alkyl groups for $R^3$ are the $C_{3-8}$ alkyl groups.

Particular values of $R^2$ within the present invention include phenylmethylamino, phenylethylamino, phenylpropylamino, 4-aminosulphonylphenylmethylamino, 4-methoxyphenylmethylamino, n-butylamino, n-hexylamino, 3-methoxypropyl-1-amino, and ethylthioethylamino.

Further particular values of $R^2$ within the present invention include butanoamido and benzoylamido.

Particular compounds within formula (I) include:

6β-[D-2-(2-benzylamino-4-hydroxypryrimidine-5-carbonylamino)-2-phenyl] acetamido penicillanic acid;

6β-[D-2-(3-(3-methoxypropyl-1-amino)-4-hydroxypyrimidine-5-carbonylamino)-2-phenyl] acetamido penicillanic acid;

6β-[D-2-(2-(3-phenylpropyl-1-amino)-4-hydroxypyrimidine-5-carbonylamino)-2-phenyl] acetamido penicillanic acid;

6β-[D-2-(2-phenylethyl-1-amino)-4-hydroxypyrimidine-5-carbonylamino-2-(4-hydroxyphenyl)-]acetamido penicillanic acid;

6β-[D-2-(2-n-butylamino)-4-hydroxypyrimidine-5-carbonylamino-2-phenyl] acetamido penicillanic acid;

6β-[D-2-(2-(n-hexylamino)-4-hydroxypyrimidine-5-carbonylamino)-2-phenyl] acetamido penicillanic acid; and 6β-[D-2-(2-(2-ethylthioethyl-1-amino)-4-hydroxypyrimidine-5-carbonylamino)-2-phenyl] acetamido penicillanic acid.

The compounds of formula (I) may be prepared by reacting a compound of formula (II):

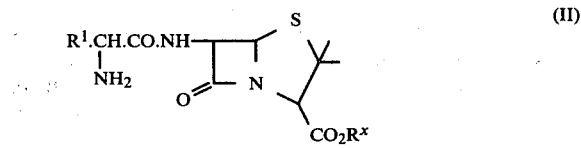

wherein the amino group is optionally substituted with a group which permits acylation to take place, R¹ is as defined with respect to formula (I) and any reactive substituents may be protected, and R$^x$ is hydrogen or a carboxyl-blocking group, with an N-acylating derivative of an acid of formula (III).

wherein R² is as defined with respect to formula (I) above and any reactive groups may be protected; and thereafter, if necessary, carrying out one or more of the following steps:
 (i) removing any carboxyl-blocking group R$^x$
 (ii) removing any protecting groups on the side chain group;
 (iii) converting the product into a salt or in vivo hydrolysable ester thereof.

Suitable groups which permit acylation to take place and which are optionally present on the amino group of the starting material of the formula (II) include N-silyl, N-stannyl and N-phosphorus groups, for example trialkylsilyl groups such as trimethylsilyl, trialkyltin groups such as tri-n-butyltin, groups of formula —P.R$^a$R$^b$ wherein R$^a$ is an alkyl, haloalkyl, aryl, aralkyl, alkoxy, haloalkyl, aryl, aralkyl, alkoxy, haloalkoxy, aryloxy, aralkyloxy, or dialkylamino group, R$^b$ is the same as R$^a$ or is halogen or R$^a$ and R$^b$ together form a ring; suitable such phosphorus groups being —P(OC$_2$H$_5$)$_2$, —P(C$_2$H$_5$)$_2$,

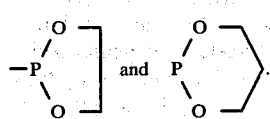

Suitable carboxyl-blocking derivatives for the group —CO$_2$R$^x$ in formula (II) include salts and ester derivatives of the carboxylic acid. The derivative is preferably one which may readily be cleaved at a later stage of the reaction. Suitable salts include metal salts, such as those with sodium, potassium and lithium, and tertiary amine salts, such as those with trilower-alkylamines, N-ethylpiperidine, 2,6-lutidine, pyridine, N-methylpyrrolidine, dimethylpiperazine. A preferred salt is with triethylamine.

Suitable ester-forming carboxyl-blocking groups are those which may be removed under conventional conditions. Such groups for R$^x$ include benzyl, p-methoxybenzyl, 2,4,6-trimethylbenzyl, 3,5-di-t-butyl-4-hydroxybenzyl, benzoylmethyl, p-nitrobenzyl, 4-pyridylmethyl, 2,2,2-trichloroethyl, 2,2,2-tribromoethyl, t-butyl, t-amyl, diphenylmethyl, triphenylmethyl, adamantyl, 2-benzyloxyphenyl, 4-methylthiophenyl, tetrahydrofur-2-yl, tetrahydropyran-2-yl, pentachlorophenyl, p-toluenesulphonylethyl, methoxymethyl, a silyl, stannyl or phosphorus-containing group, such as described above, an oxime radical of formula —N=CHR⁰ where R⁰ is aryl or heterocyclic, or an in vivo hydrolysable ester radical such as defined above.

The carboxyl group may be regenerated from any of the above esters by usual methods appropriate to the particular R$^x$ group, for example, acid- and base-catalysed hydrolysis, or by enzymically-catalysed hydrolysis, or by hydrogenation.

A reactive N-acylating derivative of the acid (III) is employed in the above process. The choice of reactive derivative will of course be influenced by the chemical nature of the substituents of the acid.

Suitable N-acylating derivatives include an acid halide, preferably the acid chloride or bromide. Acylation with an acid halide may be affected in the presence of an acid binding agent for example, tertiary amine (such as triethylamine or dimethylaniline), an inorganic base (such as calcium carbonate or sodium bicarbonate) or an oxirane, which binds hydrogen halide liberated in the acylation reaction. The oxirane is preferably a (C$_{1-6}$)-1,2,alkylene oxide—such as ethylene oxide or propylene oxide. The acylation reaction using an acid halide may be carried out at a temperature in the range —50° C. to +50° C., preferably —20° to +20° C., in aqueous or non-aqueous media such as aqueous acetone, aqueous tetrahydroform, ethyl, acetate, dimethylacetamide, dimethylformamide, acetonitrile, dichloromethane, 1,2-dichloroethane, or mixtures thereof. Alternatively, the reaction may be carried out in an unstable emulsion of water-immiscible solvent, especially an aliphatic ester or ketone, such as methyl isobutyl ketone or butyl acetate.

Alternatively, the N-acylating derivative of the acid (III) may be a symmetrical or mixed anhydride. Suitable mixed anhydrides are alkoxyformic anhydrides, or anhydrides with, for example, carbonic acid monoesters, trimethyl acetic acid, thioacetic acid, diphenylacetic acid, benzoic acid, phosphorus acids (such as phosphoric acid or phosphorous acids) or aliphatic or aromatic sulphonic acids (such as p-toluenesulphonic acid). When a symmetrical anhydride is employed, the reaction may be carried out in the presence of 2,6-lutidine as catalyst.

Alternative N-acylating derivatives of acid (III) are the acid azide, or activated esters such as esters with 2-mercaptopyridine, cyanomethanol, p-nitrophenol, 2,4-dinitrophenol, thiophenol, halophenols, including pentachlorophenol, monomethoxyphenol, N-hydroxy succinimide, or 8-hydroxyquinoline; or amides such as N-acylsaccharins or N-acylphthalimides; or an alkylidene iminoester prepared by reaction of the acid (III) with an oxime.

Other reactive N-acylating derivatives of the acid (III) include the reactive intermediates formed by reaction in situ with a condensing agent such as a carbodiimide, for example, N,N-diethyl-, dipropyl- or diisopropylcarbodiimide, N,N'-di-cyclohexylcarbodiimide, or N-ethyl-N'- -dimethylaminopropylcarbodiimide; a suitable carbonyl compound, for example, N,N'-carbonyldiimidazole or N,N'-carbonylditriazole; an isoxazolinium salt, for example, N-ethyl-5-phenylisoxazolinium-3-sulphonate or N-t-butyl-5-methylisoxazolinium perchlorate; or an N-alkoxycarbonyl 2-alkoxy-1,2-dihydroquinoline, such as N-ethoxycarbonyl 2-ethoxy-1,2-dihydroquinoline. Other condensing agents include Lewis acids (for example $BBr_3$-$C_6H_6$); or a phosphoric acid condensing agent such as diethylphosphorylcyanide. The condensation reation is preferably carried out in an organic reaction medium, for example, methylene chloride, dimethylformamide, acetonitrile, alcohol, benzene, dioxan or tetrahydrofuran.

The intermediate compound of formula (II) may be prepared by reacting a compound of formula (V):

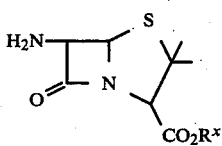

(V)

wherein the amino group is optionally substituted with a group which permits acylation to take place and $R^x$ is as defined with respect to formula (II) above, with an N-acylating derivative of an acid of formula (VI):

(VI)

wherein $R^1$ is as defined with respect to formula (I) and any reactive groups therein may be protected and $R^y$ is an amino-protecting group; and thereafter removing protecting group $R^y$.

Suitable N-acylating derivatives, carboxyl protecting groups and reaction conditions include those described hereinbefore.

Suitable amino-protecting groups $R^y$ are those well-known in the art which may be removed under conventional conditions without disruption of the remainder of the molecule.

The compounds of formula (I) may also be prepared by reacting a compound of formula (V) as described hereinbefore with an N-acylating derivative of an acid of formula (VII):

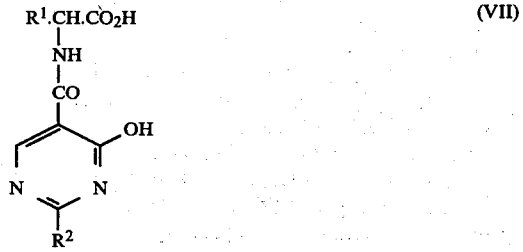

(VII)

where $R^1$ and $R^2$ are as defined with respect to formula (I) and any reactive groups therein may be protected; and thereafter, if necessary, carrying out one or more of the following steps:

(i) removing any carboxyl-blocking group $R^x$ (ii) removing any protecting groups on the side chain group;

(iii) converting the product into a salt or in vivo hydrolysable ester thereof.

The antibiotic compounds according to the invention may be formulated for administration in any convenient way for use in human or veterinary medicine, by analogy with other antibiotics, and the invention therefore includes within its scope a pharmaceutical composition comprising a compound of formula (I) above together with a pharmaceutical carrier or excipient.

The composition may be formulated for administration by any route, such as oral topical or parenteral. The compositions may be in the form of tablets, capsules, powders, granules, lozenges, creams or liquid preparations, such as oral or sterile parenteral solutions or suspensions.

Tablets and capsules for oral administration may be in unit dose presentation form, and may contain conventional excipients such as binding agents, for example syrup, acacia, gelatin, sorbitol, tragacanth, or polyvinylpyrollidone; fillers, for example lactose, sugar, maize-starch, calcium phosphate, sorbitol or glycine, tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, methyl cellulose, glucose syrup, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and if desired conventional flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampoule and sealing. Advantageously, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% by weight, preferably from 10–60% by weight, of the active material, depending on the method of administration. Where the composition comprise dosage units, each unit will preferably contain from 50–500 mg of the active ingredient. The dosage as employed for adult human treatment will preferably range from 100 to 3000 mg per day, for instance 1500 mg per day depending on the route and frequency of administration.

The compound of formula (I) may be the sole therapeutic agent in the compositions of the invention or a combination with other antibiotics or with a β-lactamase inhibitor may be employed.

Advantageously, the compositions also comprise a compound of formula (VIII) or a pharmaceutically acceptable salt or ester thereof:

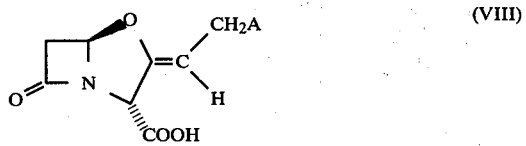

(VIII)

wherein A is hydroxyl, substituted hydroxyl, thiol, substituted thiol, amino, mono- or di-hydrocarbyl-substituted amino, or mono- or di-acylamino.

A further advantageous composition comprises a compound of formula (I) or a pharmaceutically acceptable salt or in vivo hydrolysable ester thereof together with a compound of formula (IX) or a pharmaceutically acceptable salt or in vivo hydrolysable ester thereof:

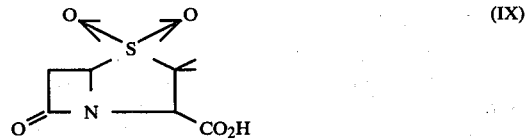

(IX)

The following Examples illustrate the preparation of the compounds of this invention.

EXAMPLE 1

Preparation of 6β-[D-2-(2-benzylamino-4-hydroxypyrimidine-5-carbonylamino)-2-phenyl]acetamido penicillanic acid (a)

2-Benzylamino-5-ethoxycarbonyl-4-hydroxypyrimidine

2-Methylthio-5-ethoxycarbonyl-4-hydroxypyrimidine (2 mmol, 428 mg) was refluxed overnight in ethanol (5 ml) with benzylamine (2 mmol, 0.22 ml, 214 mg). The title product precipitated out and was filtered off. (450 mg, 82% yield). m.p. 239°–241° C.

Found: M+, 273.1127. $C_{14}H_{15}N_3O_3$ requires M, 273.1112.

$\nu_{max}$ (Nujol) 1715 (ester C=O) cm$^{-1}$.

δ [(CD$_3$)$_2$SO] (relative to HMDS) 1.20 [3H, t, J 7.5 Hz, Ester Ethyl CH$_3$], 4.16 [2H, q, J 7.5 Hz, Ester ethyl CH$_2$], 4.60 [2H, d, J 5 Hz, Benzyl CH$_2$], 7.40 [5H, s, aromatic protons], 8.46 [1H, s, pyrimidine-6-proton], 3.5 [broad, NH and OH].

(b) 2-Benzylamino-4-hydroxypyrimidine-5-carboxylic acid

2-Benzylamino-5-ethoxycarbonyl-4-hydroxypyrimidine (4.2 mmol, 1.14 g) prepared as in (a) was hydrolysed by refluxing for 3 hours in 1 N aqueous sodium hydroxide (10 ml). On cooling and acidification to pH 2 the title product precipitated out and was filtered. (0.87 g, 85% yield).

m.p. >300° C.

δ [CF$_3$COOH] (relative to HMDS) 4.81 [2H, broad s, benzyl CH$_2$], 7.40 [5H, s, aromatic protons], 8.90 [1H, s, pyrimidine-6-proton].

(c)

6β-[D-2-(2-Benzylamino-4-hydroxypyrimidine-5-carbonylamino)-2-phenyl]acetamido penicillanic acid 2-Benzylamino-4-hydroxypyrimidine-5-carboxylic acid (0.8 mmol, 200 mg) was treated with thionyl chloride (0.8 mmol, 60 μl) in methylene chloride (MDC, 5 ml) with triethylamine (TEA, 2 mmol, 260 μl) for 1 hour at room temperature and then treated with anhydrous ampicillin (0.8 mmol, 300 mg) in MDC (8 ml) with TEA (2 mmol, 260 μl) at room temperature for 1 hour. The mixture was evaporated to dryness and then redissolved in ethyl acetate (20 ml): aqueous solution at pH 7.5 (20 ml). The aqueous phase was separated and acidified to pH 1.5 when the desired product precipitated out and was filtered off. (47 mg).

δ [CD$_3$OD] 1.47, 1.57 [6H, 2s, gem dimethyls], 4.40 [1H, s, penicillin C$_3$ proton], 4.66 [2H, s, benzyl CH$_2$], 5.55 [2H, ABq, J 4 Hz, penicillin C$_5$ and C$_6$ protons], 5.83 [1H, s, PhCHCON], 7.3–7.8 [10H, complex, aromatic protons], 8.66 [1H, s, pyrimidine C$_6$ proton].

This was converted to the disodium salt by suspending in water and adding NaHCO$_3$ (aq) with vigorous shaking until pH 6.5 was reached, followed by freeze drying of the resultant solution.

$\nu_{max}$ (Nujol) 1760 (β-lactam) cm$^{-1}$.

EXAMPLE 2

Preparation of 6β-[D-2-(2-[2-Ethylthioethyl-1-amino]-4-hydroxy pyrimidine-5-carbonylamino)-2-phenyl]acetamido penicillanic acid (a)

2-[2-(Ethylthio)ethyl-1-amino]-5-ethoxycarbonyl-4-hydroxy pyrimidine

2-Methylthio-5-ethoxycarbonyl-4-hydroxy pyrimidine (4 mmol, 856 mg) was refluxed in butanol overnight with 2-ethylthio ethylamine hydrochloride (1.0 g, 7.3 mmol). The title product was insoluble and was filtered off (0.95 g, 88%).

m.p. 189°–194° C.

Found; M+, 271.0989; $C_{11}H_{17}N_3O_3S$ requires M, 271.0987, δ [CDCl$_3$], 1.26 [3H, t, J 7.5 Hz, thioethyl CH$_3$], 1.31 [3H, t, J 7 Hz, ester ethyl CH$_3$], 2.59 [2H, q, J 7.5 Hz, thioethyl CH$_2$], 2.78 [2H, t, J 7 Hz, CH$_2$-S-Et], 3.75 [2H, d of t, Jd 9 Hz, J t 8 Hz, NHCH$_2$, collapses to t on deuteration], 4.21 [2H, q, J 7 Hz, ester ethyl CH$_2$], 8.64 [1H, s, pyrimidine C6 proton].

(b) 2-(2-(Ethylthio]ethyl-1-amino)-4-hydroxy pyrimidine-5-carboxylic acid

2-[2-(Ethylthio)ethyl-1-amino]-5-ethoxy carbonyl-4-hydroxy pyrimidine (457 mg, 1.69 mmol) was hydrolysed in boiling water for 3 hours with sodium hydroxide (200 mg, 5 mmol). Cooling and acidification yielded the title compound, (307 mg, 1.25 mmol), as a precipitate.

m.p. 188°–191° C. (d).

δ [d⁶ Acetone+D₂O], 1.27 [3H, t, J 7.5 Hz, thioethyl CH₃], 2.66 [2H, q, J 7.5 Hz, thioethyl CH₂], 2.85 [2H, t, J 7 Hz, CH₂-S-Et], 3.75 [2H, t, J 7 Hz, —N—CH₂—], 8.65 [1H, s, pyrimidine C6 proton].

(c) 6β-[D-2-(2-[2-(Ethylthio)ethyl-1-amino]-4-hydroxy pyrimidine-5-carbonylamino)-2-phenyl]acetamido penicillanic acid 2-(2-[Ethylthio]ethyl-1-amino)-4-hydroxypyrimidine-5-carboxylic acid (243 mg, 1 mmol) was coupled to ampicillin by the acid chloride route described above for Example 1(c). [174 mg, 30%].

The product possesses

δ [d⁶ acetone+D₂O], 1.20 [3H, J 7.5 Hz, thioethyl CH₃], 1.43, 1.53 [6H, 2s, gemdimethyl], 2.4–3.0 [4H, m, —CH₂—S—CH₂], 3.70 [2H, t, J 7 Hz, N—CH₂]; C₃ under HOD, 4.3; 5.4–6.0 [3H, m, α proton, C₅, C₆β-lactam protons], 7.2–7.8 [5H, m, aromatic protons], 8.56 [1H, s, pyrimidine C6 proton].

$\nu_{max}$ (Nujol) 1775 cm⁻¹ (β-lactam C=O).

EXAMPLE 3

Preparation of
6β-[D-2-(2-(3-phenylpropyl-1-amino)-4-hydroxypyrimidine-5-carbonylamino)-2-phenyl] acetamido penicillanic acid (a) 2-(3-Phenyl propyl-1-amino)-5-ethoxycarbonyl-4-hydroxypyrimidine 2-Methylthio-5-ethoxycarbonyl-4-hydroxypyrimidine (2.5 mmol, 535 mg) was refluxed in ethanol (5 ml) over 3 days with 3-phenyl propyl-1-amine (3.8 mmol, 535 μl). The title product precipitated out and was filtered off (567 mg, 75% yield).

m.p. 174°–175° C.

Found: M⁺, 301.1431; C₁₆H₁₉N₃O₃ requires M, 301.1425. δ [(CD₃)₂SO] (relative to HMDS) 1.20 [3H, t, J 7.5 Hz, ester ethyl CH₃], 1.5–2.0 [2H, m, propyl-2-CH₂] 2.63 [2H, t, J 8 Hz, propyl-3-CH₂], 3.0–3.5 [2H, broad, propyl-1-CH₂], 4.16 [2H, q, J 7.5 Hz, ester ethyl CH₂], 7.30 [5H, s, aromatic protons], 8.43 [1H, s, pyrimidine-6-proton].

(b) 2-(3-Phenyl propyl-1-amino)-4-hydroxypyrimidine-5-carboxylic acid 2-(3-Phenyl propyl-1-amino)-5-ethoxycarbonyl-4-hydroxypyrimidine (1.81 mmol, 545 mg) was hydrolysed by refluxing for 3 hours in 0.5 N aqueous sodium hydroxide (10 ml). On cooling and acidification to pH 2, the title product precipitated out and was filtered off (455 mg, 85% yield).

m.p. >300° C.

δ [CF₃COOH] (relative to HMDS) 2.16 [2H, quintet, J 6 Hz, propyl-2-CH₂], 2.80 [2H, t, J 6 Hz, propyl-3-CH₂], 3.6 [2H, broad, propyl-1-CH₂], 7.23 [5H, s, aromatic protons], 8.85 [1H, s, pyrimidine-6-proton].

(c) 6β-[D-2-(2-(3-phenylpropyl-1-amino)-4-hydroxy pyrimidine-5-carbonylamino)-2-phenyl] acetamido penicillanic acid 2-(3-Phenylpropyl-1-amino)-4-hydroxypyrimidine 5-carboxylic acid (233 mg, 0.85 mmol) was converted to the title penicillin (336 mg, 52% yield) by the method described in example 1(c).

The product possesses:

δ [(CD₃)₂CO+D₂O] 1.45, 1.55 [6H, 2s, gem dimethyl], 1.9 [2H, broad, propyl-2-CH₂], 2.73 [2H, t, J 7 Hz, propyl-3-CH₂], 3.5 [2H, broad, propyl-1-CH₂], 4.43 [1H, s, penicillin C₃ proton], 5.63 [2H, ABq, J 4 Hz, penicillin C₅ and C₆ protons], 5.91 [1H, s, PhCHCON], 7.2–7.7 [10H, complex, aromatic protons], 8.60 [1H, s, pyrimidine-6-proton].

This was converted to the disodium salt by dissolving in water by the addition of dilute sodium bicarbonate solution to pH 6.5 with vigorous shaking followed by freeze-drying.

$\nu_{max}$ (Nujol) 1760 (β-lactam) cm⁻¹.

EXAMPLE 4

Preparation of
6β-[D-2-(2-Benzylamino-4-hydroxypyrimidine-5-carbonylamino)-2-(4-hydroxyphenyl)] acetamido penicillanic acid disodium salt 2-Benzylamino-4-hydroxypyrimidine-5-carboxylic acid, prepared as in Example 1(a) and (b) (1 mmol. 245 mg), was dissolved in dry dimethylformamide (D.M.F., 3 ml) with N-hydroxysuccinimide (1.1 mmol, 126 mg) and treated overnight with dicyclohexylcarbodiimide (D.C.C., 226 mg, 1.1 mmol) in D.M.F. (0.2 ml). The suspension was cooled to 0° C. and filtered. To the solution was added amoxycillin trihydrate (420 mg, 1 mmol.) and stirring continued for 2 hours. The solution was poured dropwise into a large excess of diethylether (200 ml). The diethylether was decanted off and the precipitate washed with a further portion of ether. The solid was partitioned between aqueous NaHCO₃ (pH 7.5) and ethyl acetate. The aqueous layer was washed with 2 portions ethyl acetate and then acidified with 1 NHCl to pH 1.3. The precipitate was filtered off and this product was converted to the disodium salt by dissolving in aqueous NaHCO₃ at pH 6.5 followed by freeze drying. Yield, 180 mg (28%).

The compound possesses (free acid):

δ(d⁶ acetone and D₂O) 1.50, 1.60 (6H, 2s, gem dimethyls), 4.33 (1H, s, penicillin C₃-proton), 4.70 (2H, s, benzyl CH₂), 5.40–5.90 (3H, m, α-proton and β-lactam C₅ and C₆ protons), 6.7–7.6 (9H, m, aromatic protons), 8.56 (1H, s, pyrimidine C₆-proton).

$\nu_{max}$ (Nujol) 1760 (β-lactam) cm⁻¹.

EXAMPLE 5

Preparation of
6β-[D-2-(2-(2-phenylethyl-1-amino)-4-hydroxypyrimidine-5-carbonylamino)-2-(4-hydroxyphenyl)] acetamido penicillanic acid (a) 2-(2-Phenylethyl-1-amino)-5-ethoxycarbonyl-4-hydroxypyrimidine 2-Methylthio-5-ethoxycarbonyl-4-hydroxypyrimidine (2.5 mmol, 535 mg) was refluxed overnight in ethanol (10 ml) with 2-phenyl ethyl-1-amine (3.75 mmol, 450 mg). The title product precipitated out and was filtered off (563 mg, 77% yield).

m.p. 264°–267° C.

Found, M⁺: 287.1272; C₁₅H₁₇N₃O₃ requires M, 287.1268.

δ [CF₃COOH] (relative to HMDS) 1.37 [3H, t, J 7 Hz, ester ethyl CH₃], 3.03 [2H, t, J 6 Hz, ethylamine-2- protons], 3.7–4.1 [2H, m, ethylamine-1-protons], 4.45 [2H, q, J 7 Hz, ester ethyl, CH$_2$], 7.30 [5H, s, aromatic protons], 8.71 [1H, s, pyrimidine-6-proton].

(b)

2-(2-Phenylethyl-1-amino)-4-hydroxypyrimidine-5-carboxylic acid 2-(2-Phenylethyl-1-amino)-5-ethoxycarbonyl-4-hydroxypyrimidine (2.08 mmol), 600 mg) was hydrolysed by refluxing in 0.5 N aqueous sodium hydroxide (10 ml) for 3 hours. On cooling and acidification to pH 2 the title product precipitated out (534 mg, 98% yield). m.p. >300° C.

δ [(CD$_3$)$_2$SO] (relative to HMDS) 2.90 [2H, t, J 7 Hz, ethylamine-2-protons], 3.70 [2H, q, J 7 Hz, ethylamino-1-protons becomes t, J 7 Hz, with D$_2$O], 7.35 [5H, s, aromatic protons]8.57 [1H, s, pyrimidine-6-proton].

(c) 6β-[D-2-(2-[2-Phenylethyl-1-amino)-4-hydroxy pyrimidine-5-carbonylamino)-2-[4-hydroxyphenyl)] acetamidopenicillanic acid 2-(2-Phenylethyl-1-amino)-4-hydroxypyrimidine-5-carboxylic acid (1 mmol, 260 mg) was converted to the title penicillin (107 mg, 16% yield) by the method described in example 4. The product possesses:

δ [(CD$_3$)$_2$CO+D$_2$O] 1.51, 1.61 [6H, 2s, gem dimethyls], 3.0 [2H, m, ethylamine-2-protons], 3.7 [2H, m, ethylamine-1-protons], (C$_3$ proton obscured), 5.5–5.9 [3H, m, penicillin C$_5$ and C$_6$ protons+PhCHCON], 6.8–7.8 [9H, m, aromatic protons], 8.60 [1H, s, pyrimidine-6-proton].

This was converted to the disodium salt by dissolving in water by addition of dilute sodium bicarbonate to pH 6.5 followed by freeze drying.

$v_{max}$ (Nujol) 1760 (β-lactam) cm$^{-1}$.

EXAMPLE 6

Preparation of 6β-D-[2-(2-[4Chlorobenzylamino]-4-hydroxypyrimidine-5-carbonylamino)-2-phenyl] acetamido penicillanic acid (a)

2-(4-Chlorobenzylamino)-5-ethoxycarbonyl-4-hydroxypyrimidine

2-Methylthio-5-ethoxycarbonyl-4-hydroxypyrimidine (535 mg, 2.5 mmol) was refluxed in butanol overnight with 4-chlorobenzylamine (460 μl, 531 mg, 3.75 mmol). The product precipitated out and was filtered off (541 mg, 70% yield).

m.p. 248°–252° C. M+, 307.

δ(TFA) 1.40 (3H, t, J 7.5 Hz, ethyl CH$_3$), 4.47 (2H, q, J 7.5 Hz, ethyl CH$_2$) 4.79 (2H, d, J 3 Hz, benzyl CH$_2$), 7.38 (4H, s, aromatic protons), 8.87, 8.75 (1H, 2s, (ketoenol) pyrimidine C$_6$-proton).

(b)

2-(4-Chlorobenzylamino)-4-hydroxypyrimidine-5-carboxylic acid 2-(4-Chlorobenzylamino)-5-ethoxycarbonyl-4-hydroxypyrimidine (510 mg, 1.66 mmol) was hydrolysed in boiling water (15 ml) with NaOH (200 mg, 5 mmol) for four hours. Cooling and acidification precipitated out the title compound (466 mg, 92%).

m.p. >300° C.

δ(TFA) 4.83 (2H, s, benzyl CH$_2$), 7.40 (4H, s, aromatic protons), 8.97, 8.85 (1H, 2s, (ketoenol) pyrimidine C$_6$-proton).

(c)

6β-[D-2-(2-[4-Chlorobenzylamino]-4-hydroxypyrimidine-5-carbonylamino)-2-phenyl]acetamido penicilllanic acid 2-(4-Chlorobenzylamino)-4-hydroxypyrimidine-5-carboxylic acid (280 mg, 1 mmol) was suspended in D.M.F. with N-hydroxy succinimide (126 mg 1.1 mmol) and treated with D.C.C. (226 mg, 1.1 mmol) overnight. The suspension was cooled to 0° C. and filtered. Ampicillin (350 mg, 1 mmol) was added to the solution and stirring continued for 2 hours at room temperature. The solution was poured dropwise into ether (200 ml). The ether was decanted off and the precipitate partitioned between water (pH 7.5) and ethylacetate. The aqueous phase was washed with ethylacetate (3×25 ml) and acidified to pH 1.4. The precipitated product was filtered off and dried. (106 mg, 19%).

The product possesses:

δ (d$^6$acetone+D$_2$O) 1.50+1.60 (6H, 2s, gem dimethyls), 4.38 (1H, s, C$_3$-proton), 4.73 (2H, s, benzyl CH$_2$), 5.4–6.1 (3H, m, α-proton and C$_5$, C$_6$ β-lactam protons), 7.1–7.7 (9H, m, aromatic protons), 8.60 (1H, s, pyrimidine C$_6$-proton).

$v_{max}$ (Nujol) 1775 (β-lactam) cm$^{-1}$.

EXAMPLE 7

Preparation of 6β-[D-2-(2-[4-sulphonamidobenzylamino]-4-hydroxypyrimidine-5-carbonylamino)-2-phenyl]acetamido penicillanic acid, disodium salt (a)

2-(4-Sulphonamidobenzylamino)-5-ethoxycarbonyl-4-hydroxypyrimidine.

2-Methylthio-5-ethoxycarbonyl-4-hydroxypyrimidine (535 mg, 2.5 mmol) was refluxed in butanol over 3 days with 4-sulphonamido benzylamine hydrochloride (832 mg, 3.75 mmol). The title compound precipitated out and was washed with dilute HCl. (225 mg, 0.64 mmol). The product possesses m.p. 274°–277° C.

Found: M+, 352.0852; C$_{14}$H$_{16}$N$_4$O$_5$S requires M, 352.0863.

δ(d$^6$DMSO) 1.20 (3H, t, J 7 Hz, ethyl CH$_3$), 4.16 (2H, q, J 7 Hz, ethyl CH$_2$), 4.67 (2H, d, J 5 Hz, benzyl CH$_2$), 7.45 (2H, broad s, SO$_2$NH$_2$), 7.70 (4H, ABq, J 8 Hz, aromatic protons), 8.43 (1H, s, pyrimidine C$_6$-proton).

(b)

2-(4-Sulphonamidobenzylamino)-4-hydroxypyrimidine-5-carboxylic acid 2-(4-Sulphonamidobenzylamino)-5-ethoxycarbonyl-4-hydroxypyrimidine (225 mg, 0.64 mmol) was hydrolysed in boiling water (10 ml) with sodium hydroxide (74 mg, 1.0 mmol) for three hours. Cooling and acidification to pH 2 yielded the title compound (114 mg, 0.35 mmol).

m.p. >300° C.

δ(d$^6$DMSO) 4.79 (2H, d, J 6 Hz, benzyl CH$_2$), 7.37 (2H, broad s, SO$_2$NH$_2$), 7.70 (4H, ABq, J 8 Hz, aromatic protons), 8.49 (1H, s, pyrimidine C$_6$-proton).

(c)
6β-[D-2-(2-[4-Sulphonamidobenzylamino]-4-hydroxypyrimidine-5-carbonylamino)-2-phenyl]acetamido penicillanic acid, disodium salt 2-(4-Sulphonamidobenzylamino)-4-hydroxypyrimidine-5-carboxylic acid (105 mg, 0.32 mmol) was coupled to ampicillin by the activated ester route described above in Example 6. The product (13 mg) possesses:

δ(d⁶Acetone+D₂O) 1.50, 1.60 (6H, s, gem dimethyls), 4.36 (1H, s, C₃-proton), 4.83 (2H, s, benzyl CH₂), 5.4–6.0 (3H, m, α-proton and C₅, C₆ β-lactam protons), 7.2–8.0 (11H, m, aromatic protons and SO₂NH₂), 8.60 (1H, s, pyrimidine C₆ proton). This was converted to the disodium salt by dissolving in water with vigorous shaking by addition of sodium bicarbonate to pH 6.5 followed by freeze-drying.

$v_{max}$ (Nujol) 1760 (β-lactam) cm⁻¹.

EXAMPLE 8
Preparation of 6β-[D-2-(2[4-Hydroxy-3-methoxybenzylamino]-4-hydroxypyrimidine-5-carbonylamino)-2-phenyl] acetamido penicillanic acid, disodium salt

(a) Preparation of 2-(4-Hydroxy-3-methoxybenzylamino)-5-ethoxycarbonyl-4-hydroxypyrimidine 2-Methylthio-5-ethoxycarbonyl-4-hydroxypyrimidine (0.535 g, 2.5 mmol) was refluxed in butanol (10 ml) overnight with 4-hydroxy-3-methoxybenzylamine hydrochloride (720 mg, 3.8 mmol). The product crystallized out and was filtered off.

m.p. 181°–185° C., (375 mg).

Found: M⁺, 319.1173; C₁₅H₁₇N₃O₅ requires M⁺, 319.1180.

δ [TFA] 1.50 [3H, t, J 7 Hz, ethyl CH₃], 4.02 [3H, s, methoxy], 4.40 [2H, q, J 7 Hz, ethyl CH₂], 4.85 [2H, broad, benzyl CH₂], 7.0–7.2 [3H, m, aromatic protons], 8.83 [1H, s, pyrimidine proton].

(b) Preparation of 2-[4-Hydroxy-3-methoxybenzylamino]-4-hydroxypyrimidine-5-carboxylic acid 2-[4-Hydroxy-3-methoxybenzylamino]-5-ethoxycarbonyl-4-hydroxypyrimidine (370 mg, 1.16 mmol) was hydrolysed by refluxing in water (10 ml) with NaOH (160 mg, 4 mmol) for 2 hours. Cooling and acidification to pH 2 yielded the named product as a precipitate, (153 mg, 53% yield).

δ [d⁶DMSO] 3.77 [3H, s, methoxy], 4.50[2H, broad, benzyl CH₂], 6.7–7.0 [3H, m, aromatic protons], 8.49 [1H, s, pyrimidine proton].

(c)
6β-[D-2-(2-([4-Hydroxy-3-methoxybenzylamino]-4-hydroxypyrimidine-5-carbonylamino)-2-phenyl] acetamido penicillanic acid, sodium salt 2-(4-Hydroxy-3-methoxybenzylamino)4-hydroxypyrimidine-5-carboxylic acid was coupled to ampicillin, by the method described above in Example 6 to yield 38 mg of named product.

δ [d⁶ Acetone+D₂O] 1.50, 1.60 [6H, 2s, gem dimethyls], 3.83 [3H, s, methoxy], 4.37 [1H, s, C-3 proton], 4.60 [2H, broad s, benzyl CH₂], 5.3–6.0 [3H, m, C₅ and C₆ β-lactam protons and α proton], 6.8–7.1 [3H, m, benzyl protons], 7.2–7.7 [5H, m, phenyl protons], 8.65 [1H, s, pyrimidine-6-proton]. The product was converted to the disodium salt by dissolution of the solid, with shaking, in aqueous solution by raising the pH to 6.5 with sodium bicarbonate, followed by freeze-drying.

$v_{max}$ (Nujol) 1760 cm⁻¹ (β-lactam).

EXAMPLE 9
Preparation of 6β-[D-2-(2-[4-Methoxybenzylamino]-4-hydroxypyrimidine-5-carbonylamino)-2-phenyl] acetamido penicillanic acid

(a) 2-(4-Methoxybenzylamino)-5-ethoxycarbonyl-4-hydroxypyrimidine

2-Methylthio-5-ethoxycarbonyl-4-hydroxypyrimidine (0.535 g, 2.5 mmol) was refluxed overnight in ethanol with 4-methoxybenzylamine (510 mg, 485 μl, 3.75 mmol). The product precipitated out and was filtered off (447 mg, 59% yield).

m.p. 238°–240° C.

Found: M⁺, 303.1200. C₁₅H₁₇N₃O₄ requires M, 303.1183.

δ(TFA) 1.43 (3H, t, J 7.5 Hz, ethyl CH₃), 4.00 (3H, s, methoxy), 4.50 (2H, d, J 7.5 Hz, ethyl CH₂), 4.80 (2H, d, J 4 Hz, benzyl CH₂, coupled to NH), 7.23 (4H, ABq, J 8 Hz, aromatic protons), 8.80, 8.97 (1H, 2s, pyrimidine C₆-proton showing keto-enol tautomerism).

(b) 2-[4-Methoxybenzylamino]-4-hydroxypyrimidine-5-carboxylic acid 2-(4-Methoxybenzylamino)-5-ethoxycarbonyl-4-hydroxypyrimidine (413 mg, 1.33 mmol) was hydrolysed in refluxing water for three hours with sodium hydroxide (140 mg, 3.4 mmol); cooling and acidification to pH 2 precipitated the title compound which was filtered off. (358 mg, 94%).

m.p. >300° C.

δ(d⁶ DMSO) 3.75 (3H, s, methoxy protons), 4.54 (2H, d, J 5 Hz, benzyl CH₂), 7.17 (4H, ABq, J 8.5 Hz, aromatic protons), 8.55 (1H, s, pyrimidine C₆-proton).

(c)
6β-[D-2-(2-[4-Methoxybenzylamino]-4-hydroxypyrimidine-5-carbonylamino)-2-phenyl] acetamido penicillanic acid, disodium salt 2-(4-Methoxybenzylamino)-4-hydroxypyrimidine-5-carboxylic acid (275 mg, 1 mmol) was coupled to ampicillin by the acid chloride route described in Example 1(c) above. The crude product was columned on SiO₂ in ethylacetate:isopropyl alcohol:H₂O=5:4:1. The fractions were evaporated and then extracted into ethylacetate after layering with dilute HCl at pH 1.5 to yield pure penicillin, 43 mg.

δ(D⁶-Acetone+D₂O) 1.50, 1.60 (6H, 2s, gem dimethyls), 3.80 (3H, s, methoxy), 4.40 (1H, s, penicillin C₃-proton), 4.63 (2H, s, benzyl CH₂), 5.4–6.1 (3H, m, α-proton and C₅ and C₆ β-lactam protons), 6.8–7.7 (9H, m, aromatic protons) 8.63 (1H, s, pyrimidine C₆-proton).

The product was converted to the disodium salt by the method described above in Example 1(c).

$v_{max}$ (Nujol) 1775 (β-lactam) cm⁻¹.

EXAMPLE 10

Preparation of 6β-[D-2-(2-Furfurylamino-4-hydroxypyrimidine-5-carbonylamino)-2-phenyl] acetamido penicillanic acid, disodium salt (a) 2-Furfurylamino-5-ethoxycarbonyl-4-hydroxypyrimidine 2-Methylthio-5-ethoxycarbonyl-4-hydroxypyrimidine (535 mg, 2.5 mmol) was refluxed in butanol overnight with furfurylamine (335 μl, 3.8 mmol). The named product crystallized out and was filtered off (577 mg, 88%).

m.p. 232°–235° C.

Found: M+, 263.0912. $C_{12}H_{13}N_3O_4$ requires M+, 263.0918.

δ [d⁶DMSO] 1.23 [3H, t, J 7 Hz, ethyl $CH_3$], 4.16 [2H, q, J 7 Hz, ethyl $CH_2$], 4.70 [2H, broad→sharp+$D_2O$, furfuryl $CH_2$ protons], 6.3 [2H, m, furyl 3 and 4 protons], 7.6 [1H, m, furyl 5 proton], 8.43 [1H, s, pyrimidine-6-proton].

(b) 2-Furfurylamino-4-hydroxypyrimidine-5-carboxylic acid

2-Furfurylamino-5-ethoxycarbonyl-4-hydroxypyrimidine (526 mg, 2 mmol) was hydrolysed in water (10 ml) with NaOH (5 mmol, 200 mg) by refluxing for 3 h. Cooling and acidification to pH 2 yielded the named product as a precipitate. (435 mg, 93% yield).

δ [d⁶DMSO] 4.6 [2H, broad, furfuryl $CH_2$], 6.4 [2H, m, furyl 3 and 4 protons], 7.6 [1H, m, furyl 5 proton], 8.0 [1H, broad, NH], 8.53 [1H, s, pyrimidine-6-proton].

(c) 6β-[D-2-(2-Furfurylamino-4-hydroxypyrimidine-5-carbonylamino)-2-phenyl] acetamido penicillanic acid, disodium salt 2-Furfurylamino-4-hydroxypyrimidine-5-carboxylic acid (1.0 mmol) was coupled to ampicillin by the acid chloride route described above in Example 1(c). After work-up and nmr spectral analysis the penicillin was converted as in Example 1(c) to the disodium salt. (350 mg, yield 63%).

$\nu_{max}$ (Nujol) 1760 cm$^{-1}$ (β-lactam).

δ [d⁶-Acetone+$D_2O$] 1.53, 1.63 [6H, 2s, gem dimethyls], 4.43 [1H, s, C-3 proton], 4.83 [2H, s, furfuryl $CH_2$], 5.5–6.1 [3H, β-lactam protons and α-proton], 6.55 [2H, m, furyl 3 and 4 protons], 7.3–7.9 [6H, m, phenyl protons and furyl-5-proton], 8.80 [1H, s, pyrimidine-6-proton].

EXAMPLE 11

Preparation of 6β-[D-2-(2-Methylamino-4-hydroxypyrimidine-5-carboxylamino)-2-phenyl] acetamido, penicillanic acid, disodium salt (a) 2-Methylamino-5-ethoxycarbonyl-4-hydroxypyrimidine 2-Methylthio-5-ethoxycarbonyl-4-hydroxypyrimidine (214 mg, 1 mmol) was warmed to 160° C. with 1 ml methylamine acetate; after three hours, water (8 mls) was added when the product precipitated out (125 mg, 63%).

m.p. 242°–244°.

δ (d⁶-DMSO) 1.30 (3H, t, J 7 Hz, ethyl $CH_3$), 2.90 (3H, d, J 4 Hz, N-Me→s on deuteration), 4.22 (2H, q, J 7 Hz, ethyl $CH_2$), 8.57 (1H, s, pyrimidine $C_6$-proton).

(b) 2-Methylamino-4-hydroxypyrimidine-5-carboxylic acid

2-Methylamino-5-ethoxycarbonyl-4-hydroxypyrimidine (360 mg 1.9 mmol) was hydrolysed in boiling water (10 ml) with NaOH (0.19 g, 4.7 mmol) for 2 h. Cooling and acidification to pH 2 yielded the named product as a precipitate (261 mg, 80%).

m.p. 220°–222° C. (d).

δ [d⁶DMSO] 2.97 [3H, s, $NHCH_3$], 8.55 [1H, s, pyrimidine-6-proton].

(c) 6β-D-2-(2-Methylamino-4-hydroxypyrimidine-5-carbonylamino)-2-phenyl] acetamido penicillanic acid, disodium salt 2-Methylamino-4-hydroxy pyrimidine-5-carboxylic acid (1 mmol, 169 mg) was coupled to ampicillin by the acid chloride route described in Example 1(c). The product was purified by preparative T L C) to give a product of 90% purity which was converted to the disodium salt as in Example 1(c) and freeze dried (yield 11 mg). The compound possesses:

δ [$D_2O$, 250 MHz] 1.40, 1.46 [6H, 2s, gem dimethyls], 2.88 [3H, s, $NHCH_3$], 4.16 [1H, s, C-3 proton], 5.43 [2H, s, $C_5$ and $C_6$ β-lactam protons], 5.55 [1H, s, C α-proton], 7.35, 7.55 [5H, m, aromatic protons], 8.38 [1H, s, pyrimidine-6-proton].

EXAMPLE 12

Preparation of 6β-[D-2-(2[3-Methoxypropyl-1-amino]-4-hydroxypyrimidine-5-carbonylamino)-2-phenyl acetamido penicillanic acid, disodium salt (a) 2-(3-Methoxypropyl-1-amino)-5-ethoxycarbonyl-4-hydroxypyrimidine 2-Methylthio-5-ethoxycarbonyl-4-hydroxypyrimidine (535 mg, 2.5 mmol) was refluxed over 3 days in ethanol (10 ml) with 3-methoxypropylamine (350 mg, 4 mmol). The precipitated product was filtered off (435 mg, 65%).

m.p. 181°–183° C.

δ [d⁶DMSO]1.30 [3H, t, J 7 Hz, ethyl $CH_3$], 1.80 [2H, quintet, J 6 Hz, $NHCH_2CH_2CH_2OMe$], 3.1–3.8 [7H, m+s, $NHCH_2CH_2CH_2OMe$], 4.20 [2H, q, J 7 Hz, ethyl $CH_2$], 8.45 [1H, s, pyrimidine-6-proton].

Found: M+ 255.1220; $C_{11}H_{17}N_3O_4$ requires M, 255.1219.

(b) 2-(3-Methoxypropyl-1-amino)-4-hydroxy pyrimidine-5-carboxylic acid 2-(3-Methoxypropyl-1-amino)-5-ethoxycarbonyl-4-hydroxy pyrimidine (395 mg, 1.55 mmol) was hydrolysed in boiling water (10 ml) with NaOH (4 mmol) for 2 hours. Cooling and acidification to pH 2 yielded the precipitated named product (268 mg, 75%).

δ [d⁶-DMSO] 1.80 [2H, quintet, J 6 Hz, $NCH_2CH_2CH_2OMe$], 3.2–3.6 [7H, s+m, $NCH_2CH_2CH_2OMe$], 8.49 [1H, s, pyrimidine-6-proton].

(c)

6β-[D-2-(2-[3-methoxypropyl-1-amino]-4-hydroxypyrimidine-5-carbonylamino)-2-phenyl] acetamido penicillanic acid, disodium salt 2-(3-Methoxypropyl-1-amino)-4-hydroxypyrimidine-5-carboxylic acid (227 mg 1 mmol) was coupled to ampicillin by the acid chloride route as described in Example 1(c) in 30% yield. The acid was converted to the disodium salt as described in Example 1(c). The free acid showed:

δ [d⁶-Acetone+D₂O] 1.50, 1.60 [6H, 2s, gem dimethyls], 1.87 [2H, quintet, J 7 Hz, N-CH₂CH₂CH₂OMe], 3.2–3.7 [7H, s+m, NHCH₂CH₂CH₂OMe], 4.40 [1H, s, C-3 proton], 5.4–6.1 [3H, m, β-lactam+C-α protons], 7.2–7.7 [5H, m, phenylprotons], 8.60 [1H, s, pyrimidine-6-proton].

EXAMPLE 13

6β-[D-2-(2-Methoxyethyl-1-amino]-4-hydroxypyrimidine-5-carbonylamino)-2-phenyl] acetamido penicillanic acid, disodium salt (a)

2-(2-Methoxyethyl-1-amino)-5-ethoxycarbonyl-4-hydroxypyrimidine

2-Methylthio-5-ethoxycarbonyl-4-hydroxypyrimidine (535 mg, 2.5 mmol) was refluxed in ethanol overnight with 2-methoxyethylamine (4 mmol, 350 μl); the named product precipitated out and was filtered off (382 mg, 63%)

m.p. 198°–200°.

Found: M⁺, 241 1077; C₁₀H₁₅N₃O₄ requires M⁺, 241 1063.

δ [d⁶DMSO] 1.20 [3H, t, ethyl CH₃], 3.0–3.7 [7H, s+m, N-CH₂CH₂OMe], 4.13 [2H, q, ethyl CH₂], 8.33 [1H, s, pyrimidine-6-proton].

(b)

2-(2-Methoxyethyl-1-amino)-4-hydroxypyrimidine-5-carboxylic acid 2-(2-Methoxyethyl-1-amino)-5-ethoxycarbonyl-4-hydroxypyrimidine (345 mg, 1.43 mmol) was hydrolysed in water with NaOH (4 mmol, 160 mg), by refluxing for 2 h. Cooling and acidification to pH 2 yielded precipitated named product (247 mg, 72%).

δ [d⁶DMSO] 3.3–3.7 [7H, s+m, NCH₂CH₂OMe], 8.50 [1H, s, pyrimidine-6-proton].

(c)

6β-[D-2-[2-Methoxyethyl-1-amino]-4-hydroxypyrimidine-5-carbonylamino)-2-phenyl] acetamido penicillanic acid, disodium salt 2-(2-Methoxyethyl-1-amino)-4-hydroxypyrimidine-5-carboxylic acid (213 mg, 1 mmol) was coupled to ampicillin by the acid chloride route as described in Example 1(c) in 48% yield. The free acid showed:

δ [d⁶Acetone+D₂O] 1.50, 1.60 [6H, 2s, gem dimethyls], 3.40 [3H, s, OMe], 3.6 [4H, m, N-CH₂CH₂-O], 4.33 [1H, s, C-3 proton], 5.4–6.0 [3H, m, C-5 and C-6 β-lactam+α-protons], 7.2–7.7 [5H, m, phenyl protons], 8.50 [1H, s, pyrimidine-6-proton]. Conversion to the disodium salt as in Example 1(c) gave the title product ν_max (Nujol) 1765 cm⁻¹.

EXAMPLE 14

Preparation of 6β-[D-2-(2-[2-(ethylthio) ethyl-1-amino]-4-hydroxypyrimidine-5-carbonylamino)-2-(4-hydroxyphenyl)]acetamidopenicillanic acid, disodium salt 2-(2-[Ethylthio]ethyl-1-amino)-4-hydroxypyrimidine-5-carboxylic acid, prepared as in Example 2, (243 mg, 1 mmol) was dissolved in MDC (4 ml) with triethylamine (290 μl, 2.2 mmol) and cooled to −20° C. Thionyl chloride (75 μl, 1 mmol) was added and the solution stirred for 1 hour. Amoxycillin trihydrate (420 mg, 1 mmol) was stirred in MDC (8 ml) with triethylamine (290 μl, 2.2 mmol) and cooled to −20° C. The acid chloride solution was then added and stirring continued for 2¼ hours. The MDC was evaporated off and the product, partitioned between water (pH 7.5) and ethyl acetate. After washing the aqueous phase with further ethylacetate, the aqueous phase was acidified to pH 1.3. The precipitated product was filtered off and dried (197 mg, 33%). After NMR analysis the acid was converted to the disodium salt in the usual way.

δ [d⁶Acetone+D₂O] (free acid) 1.23 [3H, t, J 7 Hz, S-CH₂CH₃], 1.50, 1.60, [6H, 2s, gemdimethyls], 2.3–3.0 [4H, m, N-CH₂CH₂SCH₂CH₃], 3.5–3.8 [2H, m, N-CH₂-CH₂-S], 4.32 [1H, s, proton], 5.4–5.8 [3H, m, C-5 and C-6 β-lactam, Cα-protons], 7.07 [4H, ABq, J 7 Hz, phenyl protons], 8.50 [1H, s, pyrimidine C-6 proton].

EXAMPLE 15

Preparation of 6β-[D-2-(2-n-propylamino-4-hydroxypyrimidine-5-carbonylamino)-2-phenyl] acetamido penicillanic acid, disodium salt (a)

2-n-Propylamino-5-ethoxycarbonyl-4-hydroxypyrimidine

2-Methylthio-5-ethoxycarbonyl-4-hydroxypyrimidine (2 mmol, 428 mg) was heated on an oil bath at 160° C. with n-propylamine acetate (1 ml) for 1 hour. The semi solid was cooled and then treated with 50 ml boiling water, and the solid product was filtered off (yield 400 mg, 88%)

m.p. 203°–208° C.

δ (CDCL₃+D₂O) 0.95 (3H, t, J 7 Hz, NCH₂CH₂CH₃) 1.36 (3H, t, J 7 Hz, ethyl CH₃), 1.71 (2H, m, NCH₂CH₂CH₃), 3.60 (2H, t, J 6.5 Hz, N-CH₂CH₂CH₃), 4.30 (2H, q, J 7 Hz, ethyl CH₂), 8.80 (1H, s, pyrimidine-6-proton).

(b) 2-n-Propylamino-4-hydroxypyrimidine-5-carboxylic acid 2-n-Propylamino-5-ethoxycarbonyl-4-hydroxypyrimidine (380 mg, 1.75 mmol) was hydrolysed in boiling water with NaOH (4 mmol, 160 mg) for 2 hours. Cooling and acidification to pH 2 precipitated the title acid (289 mg, 84%).

δ (d⁶DMSO+CD₃OD+D₂O) 0.97 (3H, t, J 6.5 Hz, NCH₂CH₂CH₃), 1.63 (2H, sextet, J 6.5 Hz, NCH₂CH₂CH₃), 3.40 (2H, t, J 6.5 Hz, N-CH₂CH₂CH₃), 8.50 (1H, s, pyrimidine C-6 proton).

(c)

6β-[D-2-(2-n-propylamino-4-hydroxypyrimidine-5-carbonylamino)-2-phenyl] acetamido penicillanic acid, disodium salt 2-n-Propylamino-4-hydroxypyrimidine-5-carboxylic acid (197 mg, 1 mmol) was coupled to ampicillin by the acid chloride route described above in Example 1(c). The free acid product (0.27 g, 47%) possessed:

δ (d⁶Acetone+D₂O) 1.00 (3H, t J 6Hz, NCH₂CN₂$_{CH3}$), 1.53, 1.63 (6H, 2s, gemdimethyls), 1.2–1.8 (2H, m obscured by gemdimethyls, NCH₂CH₂CH₃), 3.43 (2H, t, J 6.5 Hz, N-CH₂CH₂CH₃), 4.42 (1H, s, C-3 proton), 5.58(2H, ABq, J 4 Hz, C-5 and C-6 β-lactam protons), 5.90 (1H, s, C-α proton), 7.3–7.7 (5H, m, aromatic protons), 8.58 (1H, s, pyrimidine C-6 proton).

The acid was converted to the disodium salt in the usual way.

EXAMPLE 16

Preparation of 6β-[D-2-(2-n-Butylamino-4-hydroxypyrimidine-5-carbonylamino)-2-phenyl] acetamido penicillanic acid, disodium salt (a)

2-n-Butylamino-5-ethoxycarbonyl-4-hydroxypyrimidine

2-Methylthio-5-ethoxycarbonyl-4-hydroxypyrimidine (2.5 mmol, 535 mg) was refluxed overnight in ethanol (10 ml) with butylamine (0.4 ml, 4 mmol). The solution was cooled and the product filtered off (Yield 462 mg, 77%)

m.p. 198°–201° C.

δ [d⁶DMSO] 0.95 (3H, m, CH₂CH₂CH₃), 1.30 (3H, t, J 7 Hz, ethyl CH₃), 1.2–1.8 (4H, m, N-CH₂CH₂CH₂CH₃), 3.5 (2H, broad, N-CH₂CH₂), 4.25 (2H, q, J 7 Hz, ethyl CH₂), 8.53 (1H, s, pyrimidine C-6 proton).

(b) 2-n-Butylamino-4-hydroxypyrimidine-5-carboxylic acid 2-n-Butylamino-5-ethoxycarbonyl-4-hydroxypyrimidine (1.75 mmol, 420 mg) was hydrolysed with NaOH (5 mmol, 200 mg) in boiling water (10 ml) for 2 hours. Cooling and acidification to pH 2 precipitated the title acid (234 mg, 63%).

δ [DMSO+D₂O] 0.7–1.6 [7H, broad, N-CH₂CH₂CH₂CH₃], 3.35 [2H, broad, N-CH₂-], 8.45 [1H, s, pyrimidine C-6 proton].

(c)

6β-[D-2-(2-n-Butylamino-4-hydroxypyrimidine-5-carbonylamino)-2-phenyl] acetamido penicillanic acid, disodium salt 2-n-Butylamino-4-hydroxypyrimidine-5-carboxylic acid (211 mg, 1 mmol) was coupled to ampicillin by the acid chloride route described above in Example 1(c), yielding 190 mg (35%) of the title penicillin, subsequently converted to the disodium salt in the usual way.

δ (d⁶Acetone+D₂O) (free acid) 0.8–1.9 (7H, NCH₂CH₂CH₂CH₃) 1.53+1.63 6H, 2s, gemdimethyls, 3.4–3.6 (2H, broad, N—CH₂—) 4.33 (1H, s, C-3 proton), 5.3–6.1 (3H, m, C-5 and C-6 β-lactam+C-α protons) 7.2–7.7 (5H, m, phenyl protons), 8.51 (1H, s, pyrimidine C-6 proton).

EXAMPLE 17

Preparation of 6β-[D-2-(2-n-Butylamino-4-hydroxypyrimidine-5-carbonylamino)-2-(4-hydroxyphenyl)] acetamido penicillanic acid, disodium salt 2-n-Butylamino-4-hydroxypyrimidine-5-carboxylic acid, (239 mg, 1 mmol) prepared as in Example 16 (a) and (b), was coupled to amoxycillin trihydrate by the acid chloride route described in Example 14 to yield, after the usual workup, 51 mg of the penicillin disodium salt.

δ (d⁶Acetone+D₂O) (free acid) 0.7–2.0 (7H, m, NCH₂CH₂CH₂CH₃), 1.40, 1.50 (6H, 2s, gemdimethyls), 3.33 (2H, t, J 6 Hz, N-CH₂-) 4.13 (1H, s, C-3 proton), 5.3–5.8 (3H, m, C-5 and C-6 β-lactam and C-α protons), 6.95 (4H, ABq, J 8 Hz, aromatic protons), 8.32 (1H, s, C-6 pyrimidine proton).

EXAMPLE 18

Preparation of 6β-[D-2-(2-n-Pentylamino-4-hydroxypyrimidine-5-carbonylamino)-2-phenyl] acetamido penicillanic acid, disodium salt (a)

2-n-Pentylamino-5-ethoxycarbonyl-4-hydroxypyrimidine

2-Methylthio-5-ethoxycarbonyl-4-hydroxypyrimidine (2.5 mmol, 535 mg) was refluxed overnight in butanol with n-pentylamine (600 μl, 5 mmol). On cooling, the precipitated product was filtered off (340 mg, 54%) m.p. 166°–170° C.

δ(CDCl₃) 0.7–1.7 (9H, m, NCH₂CH₂CH₂CH₂CH₃), 1.15 (3H, t, J 7 Hz, ethyl CH₃), 3.60 (2H, t, J 7 Hz, N—CH₂—), 4.23 (2H, q, J 7 Hz, ethyl CH₂), 8.67 (1H, s, 6-H, pyrimidine).

(b) 2-n-Pentylamino-4-hydroxypyrimidine-5-carboxylic acid 2-n-Pentylamino-5-ethoxycarbonyl-4-hydroxypyrimidine (333 mg, 1.3 mmol) was hydrolysed with NaOH (4 mmol, 160 mg) in boiling water for 90 minutes. Cooling and acidification to pH 2 yielded the title acid as a precipitate, (252 mg, 86%).

δ (CDCl₃) 0.7–1.7 (9H, m, NCH₂ (CH₂)₃CH₃), 3.50 (2H, t, J 7 Hz, N—CH₂—), 8.75 (1H, s, pyrimidine C-6 proton).

(c)

6β-[D-2-(2-n-Pentylamino-4-hydroxypyrimidine-5-carbonylamino)-2-phenyl] acetamido penicillanic acid, disodium salt 2-n-Pentylamino-4-hydroxypyrimidine-5-carboxylic acid (225 mg, 1 mmol) was coupled to ampicillin by the acid chloride route described in Example 1(c) to give the title product (367 mg, 66% yield), converted to the disodium salt in the usual way.

δ (d⁶Acetone+D₂O) (free acid) 0.7–1.9 (9H, m, N—CH₂—(CH₂)₃CH₃), 1.53, 1.63 (6H, 2s, gemdimethyls), 3.6 (2H, m, N-CH₂), (C-3 proton under HOD), 5.75 (2H, ABq, J=4 Hz, C-5 and C-6 β-lactam protons), 6.15 (1H, s, C-α proton), 7.3–7.8 (5H, m, aromatic protons), 8.8 (1H, s, pyrimidine C-6 proton).

ν$_{max}$ (Nujol) 1760 (β-lactam) cm⁻¹.

EXAMPLE 19

Preparation of
6β-[D-2-(2-n-hexylamino-4-hydroxypyrimidine-5-carbonylamino)-2-phenyl] acetamido penicillanic acid, disodium salt (a) 2-n-Hexylamino-4-hydroxypyrimidine 2-Methylthio-5-ethoxycarbonyl-4-hydroxypyrimidine (535 mg, 2.5 mmol) was refluxed overnight in ethanol with n-hexylamine (500 μl, 3.8 mmol). The product was filtered off and washed with ethanol. (Yield: 478 mg, 71%).

m.p. 166°–169° C.

δ (CDCl$_3$) 0.6–1.7 (14H, m, NHCH$_2$—(—CH$_2$—)$_4$—CH$_3$+Ethyl CH$_3$), 2.83 (2H, t, J 6.5 Hz, N—CH$_2$—), 4.28 (2H, q, J 7 Hz, Ethyl CH$_2$), 8.70 (1H, s, pyrimidine C-6 proton).

(b) 2-n-Hexylamino-4-hydroxy pyrimidine-5-carboxylic acid 2-n-Hexylamino-5-ethoxycarbonyl-4-hydroxypyrimidine pyrimidine (470 mg, 1.75 mmol) was hydrolysed in boiling water with NaOH (190 mg, 4.75 mmol) for 2½ hours. Cooling and acidification to pH 2 precipitated the title acid, (278 mg, 66%).

δ (CDCl$_3$+CD$_3$OD) 0.8–1.7 (11H, m, NHCH$_2$—(CH$_2$)$_4$—CH$_3$), 3.4 (2H, broad, N—CH$_2$—), 8.63 (1H, s, pyrimidine C$_6$-proton).

(c) 6β-(D-2-(2-n-Hexylamino-4-hydroxypyrimidine-5-carbonylamino)2-phenyl] acetamido penicillanic acid, disodium salt 2-n-Hexylamino-4-hydroxypyrimidine-5-carboxylic acid (1 mmol, 239 mg) was coupled to ampicillin by the acid chloride route described in Example 1(c) to yield the title penicillin free acid (318 mg, 56%) converted to the disodium salt in the usual way.

δ (d$^6$Acetone+D$_2$O) (free acid) 0.7–1.9 (11H, m, N—CH$_2$—(CH$_2$)$_4$—CH$_3$), 1.50, 1.60 (6H, 2s, gemdimethyls), 3.50 (2H, t, J 7 Hz, N—CH$_2$—), 4.40 (1H, s, C—3 proton), 5.60 (2H, ABq, J 4 Hz, C-5 and C-6 β-lactam protons), 5.97 (1H, s, C-α proton), 7.2–7.7 (5H, m, aromatic protons), 8.58 (1H, s C$_6$-pyrimidine proton).

EXAMPLE 20

Preparation of
6β-[D-2-(2-n-Octylamino-4-hydroxypyrimidine-5-carbonylamino)-2-phenyl] acetamido penicillanic acid, disodium salt (a) 2-n-Octylamino-5-ethoxycarbonyl-4-hydroxypyrimidine 2-Methylthio-5-ethoxycarbonyl-4-hydroxypyrimidine (2.5 mmol, 535 mg) was refluxed overnight in ethanol with n-octylamine (4 mmol, 650 μl). The product was filtered off and washed with ethanol. Yield 402 mg (54.5%)

m.p. 135°–138° C.

δ (CDCl$_3$) 0.6–1.8 (18H, m, NHCH$_2$—(CH$_2$)$_6$-CH$_3$+ethyl CH$_3$), 3.55 (2H, broad, N—CH$_2$), 4.22(2H, q, J 7 Hz, ethyl CH$_2$), 8.63 (1H, s, C-6 pyrimidine proton).

(b) 2-n-Octylamino-4-hydroxypyrimidine-5-carboxylic acid, 2-n-Octylamino-5-ethoxycarbonyl-4-hydroxypyrimidine (400 mg, 1.4 mmol) was hydrolysed in boiling water (10 ml): ethanol (3 ml) with NaOH (5 mmol, 200 mg).

The product was filtered at pH 2 and recrystallised from methanol to remove traces of ester. Yield 133 mg (35%).

δ (d$^6$DMSO) 0.7–1.8 (15H, m, N—CH$_2$—CH$_2$—)$_6$—CH$_3$) 3.2–3.7 (3H, broad, NH—CH$_2$—), 8.50(1H, s, C-6 pyrimidine proton).

(c) 6β-[D-2-(2-n-Octylamino-4-hydroxypyrimidine-5-carbonylamino)-2-phenyl] acetamido penicillanic acid, disodium salt 2-n-Octylamino-4-hydroxypyrimidine-5-carboxylic acid (b 0.5 mmol, 133 mg) was coupled to ampicillin by the acid chloride route described above in Example 1(c), and then treated with 2 equivalents Sodium ethyl hexanoate (SEH) in methyl isobutyl ketone (MIBK) to prepare the title disodium salt (51 mg).

δ (d$^6$Acetone+D$_2$O) (free acid) 0.8–1.7 (21H, m, gemdimethyls+N—CH$_2$—(CH$_2$)$_6$—CH$_3$), 3.2–3.5(2H, m, N—CH$_2$—), (C-3 proton obscured by HOD), 5.5–6.1 (3H, m, C-5 and C-6 β-lactam protons+C-α protons), 7.3–7.8 (5H, m, aromatic protons), 8.55 (1H, s, C-6 pyrimidine proton).

ν$_{max}$ (Nujol) 1770 (β-lactam) cm$^{-1}$.

EXAMPLE 21

Preparation of
6β-[D-2-(2-Allylamino-4-hydroxypyrimidine-5-carbonylamino)2-phenyl] acetamido penicillanic acid, disodium salt (a) 2-Allylamino-5-ethoxycarbonyl-4-hydroxypyrimidine 2-Methylthio-5-ethoxycarbonyl-4-hydroxy pyrimidine (2.5 mmol, 535 mg) was refluxed in ethanol overnight with allylamine (760 μl, 10 mmol). The product was filtered off and washed with ethanol. Yield 518 mg (93%).

m.p. 222°–226° C.

δ (CDCl$_3$+CD$_3$OD) 1.35 (3H, t, J 7 Hz, ethyl CH$_3$), 3.35 (2H, d, J 5.5 Hz, N—CH$_2$—CH=), 4.33 (2H, q, J 7 Hz, ethyl CH$_2$), 5.12 (1H, m, transolefinic proton), 5.31 (1H, d of m, cisolefinic proton), 5.7–6.4 (1H, m, N—CH$_2$—CH=CH$_2$), 8.73 (1H, s, pyrimidine C-6 proton).

(b) 2-Allylamino-4-hydroxypyrimidine-5-carboxylic acid

2-Allylamino-5-ethoxycarbonyl-4-hydroxypyrimidine (585 mg, 2.5 mmol) was hydrolysed in boiling water with NaOH (300 mg, 7.5 mmol) for 2 hours. Cooling and acidification to pH 2 yielded the title acid (321 mg, 66%).

δ (d$^6$DMSO+CD$_3$OD) 4.1 (2H, broad, N—CH$_2$), 5–14(1H, m, transolefinic proton), 5.37 (1H, d of m, J″d″=5 Hz, cisolefinic proton), 5.7–6.4 (1H, m, N—CH$_2$—CH=CH$_2$).

(c)
6β-[D-2-(2-Allylamino-4-hydroxypyrimidine-5-carbonylamino)-2-phenyl] acetamido penicillanic acid, disodium salt 2-Allylamino-4-hydroxypyrimidine-5-carboxylic acid (195 mg, 1 mmol) was coupled to ampicillin by the acid chloride route described in Example 1(c) above yielding the named penicillin (100 mg, 19%).

δ (d⁶Acetone+D₂O) 1.55, 1.65 (6H, 2s, gemdimethyls), 4.15 (2H, m, N—CH₂—), 4.47 (1H, s, C-3 proton), 5.15 (1H, m, transolefinic proton), 5.37 (1H, d cf m, cisolefinic proton), 5.4–6.4 (4H, m, C-5 and C-6 β-lactam, C-α and —NHCH₂CH= protons), 7.3–7.7 (5H, m, aromatic protons), 8.63 (1H, s, C-6 pyrimidine proton). The free acid was converted to the disodium salt by dissolution of the solid in aqueous solution at pH 6.5, obtained by addition of sodium bicarbonate solution, and freeze-drying.

EXAMPLE 22

Preparation of 6β-[D-2-(2-n-butyrylamino-4-hydroxypyrimidine-5-carbonylamino)-2-phenyl] acetamido penicillanic acid, disodium salt (a) 2-n-Butyrylamino-4-hydroxypyrimidine-5-carboxylic acid 2-Amino-4-hydroxypyrimidine-5-carboxylic acid (310 mg, 2 mmol) was suspended in chloroform (20 ml) and treated with triethylamine (880 μl, 6.2 mmol) and trimethylsilyl chloride (850 μl, 6.2 mmol) at reflux for 3½ hours. n-Butyrychloride (2.2 mmol, 220 μl) was added and refluxing continued for 2 hours. The solution was allowed to cool down overnight and then water (10 ml) added. The solid was dissolved in the aqueous layer by addition of NaOH. The aqueous layer was washed with chloroform and then the product was precipitated out by acidification to pH 0. The solid was filtered and washed with ether. Yield 157 mg (34%).

m.p. 245°–247° C. (d).

δ (d⁶DMSO) 1.00 (3H, t, J 7 Hz, CH₂CH₂CH₃), 1.8 (2H, m, CH₂CH₂CH₃) 2.57 (2H, t, J 7 Hz, COCH₂CH₂CH₃), 8.70 (1H, s, C-6 pyrimidine proton).

(b) 6β-[D,2-((2-n-Butyrylamino-4-hydroxy pyrimidine-5-carbonylamino)2-phenyl] acetamido penicillanic acid, disodium salt 2-n-Butyrylamino-4-hydroxypyrimidine-5-carboxylic acid (225 mg, 1 mmol) was coupled to ampicillin by the acid chloride route described above in Example 1(c). The crude product was purified by T[L]C] on silica (elution with ethyl acetate (5):isopropyl alcohol (4):water (1)), and the desired fraction reworked through aqueous bicarbonate, acidified and filtered as the solid free acid before converting to the disodium salt by dissolution of the solid in water by the addition of sodium bicarbonate solution to pH 6.5 and shaking, followed by freeze-drying (55 mg).

δ (D₂O) 0.98 (3H, t, J 7 Hz, CDCH₂CH₂CH₃), 1.3–1.9 (2H, m, COCH₂CH₂CH₃), 1.43, 1.50 (6H, 2s, gemdimethyls), 2.47 (2H, t, J 7 Hz, COCH₂CH₂CH₃), 4.20 (1H, s, C-3 proton), 5.45 (2H, accidental singlet, C-5 and C-6 β-lactam protons), 5.63 (1H, s, C-α), 7.3–7.6 (5H, m, aromatic protons), 8.50 (1H, s, C-6 pyrimidine proton).

EXAMPLE 23

Preparation of 6β-[D-2-(2-benzoylamino-4-hydroxypyrimidine-5-carbonylamino)-2-phenyl] acetamido penicillanic acid, disodium salt (a) 2-Benzoylamino-4-hydroxypyrimidine-5-carboxylic acid 2-Amino-4-hydroxypyrimidine-5-carboxylic acid (310 mg, 2 mmol) was suspended in chloroform (20 ml) and treated with triethylamine (880 μl, 6.2 mmol) and trimethylsilylchloride (850 μl, 6.2 mmol) at reflux for 4 hours. Benzoyl chloride (250 μl, 2 mmol) was added and the reaction mixture allowed to cool overnight. Water (10 ml) was added with very vigorous stirring and the solid product was dissolved in the aqueous layer by addition of 10% NaOH. After washing the aqueous layer with further chloroform, the product was precipitated by acidification to pH 0. The filtered product was washed with water and ether. Yield 374 mg (72%)

m.p. 252°–254° C. (d).

δ [d₆DMSO] 7.5–8.4 [3H+2H, m+m, aromatic protons] 8.7 [1H, s, C-6 pyrimidine proton].

(b) 6β-[D,2-(2-Benzoylamino-4-hydroxypyrimidine-5-carbonylamino)-2-phenyl] acetamido penicillanic acid, disodium salt 2-Benzoylamino-4-hydroxypyrimidine-5 carboxylic acid (259 mg, 1 mmol) was coupled to ampicillin by the acid chloride route described above in Example 1(c). The crude product was eluted from silica with 5:4:1 ethylacetate:isopropylalcohol:water and then reworked through aqueous bicarbonate followed by filtration of the solid precipitated at pH 1.3 (74 mg, 12%).

δ (d⁶Acetone+D₂O) 1.47, 1.57 (6H, 2s, gemdimethyls), 4.33 (1H, s, C-3 proton), 5.55 (2H, ABq J 4 Hz, C-5 and C-6 β-lactam protons), 5.90 (1H, s, C-α-proton), 7.2–8.2 (10H, m, aromatic protons), 8.65 (1H, s, pyrimidine C-6 proton).

The free acid was converted to the disodium salt as in Example 22.

EXAMPLE 24

Preparation of 6β-D-2-(2-Isobutyloxycarbonylamino-4-hydroxypyrimidine-5-carbonylamino)-2-phenyl]acetamido penicillanic acid, disodium salt 2-Amino-4-hydroxypyrimidine-5-carboxylic acid (155 mg, 1 mmol) was dissolved in D.M.F. (3 ml) with triethylamine (140 μl, 1 mmol), and then cooled to −10° C. and treated with isobutylchloroformate (136 μl, 1.1 mmol) for 1 hour. Ampicillin (350 mg, 1 mmol) in D.M.F. (3 ml) with triethylamine (140 μl, 1 mmol) was cooled to −10° C. and the above activated acid solution run in. After 90 mins., allowing to warm to room temperature, the solution was poured dropwise into ether (250 ml) and the solid filtered off. The solid was partitioned between water/ethylacetate at pH 7.5. The aqueous layer was washed with ethylacetate (3×20 ml) and acidified to pH 1.3. The solid product was filtered off and washed with water. (Yield 110 mg, 18%).

δ (d⁶Acetone+D₂O) 0.9, 1.0 (6H, 2s, —O—CH₂CH(CH₃)₂), 1.65, 1.75 (6H, 2s, gemdimethyls), 1.9 (1H, m, OO—CH₂CH(CH₃)₂), 3.95 (1H, s, C-3 proton), 4.10 (2H, d, J 6 Hz, O—CH₂CH), 5.50 (2H, ABq, J 4 Hz, C-5 and C-6 β-lactam protons), 5.80 (1H, s, C-α protons), 7.2–7.6 (5H, m, aromatic protons), 8.50 (1H, s, pyrimidine C-6 proton).

The free acid was converted to the disodium salt as in Example 22.

EXAMPLE 25

Preparation of 6β-D-2-(2-benzyloxycarbonylamino-4-hydroxypyrimidine-5-carbonylamino-2-phenyl] acetamido penicillanic acid, disodium salt 2-Amino-4-hydroxypyrimidine-5-carboxylic acid (155 mg, 1.0 mmol) was dissolved in D.M.F. (3 ml) with triethylamine (430 μl, 3.1 mmol) and cooled to −10° C. Benzylchloroformate (300 μl, 2.2 mmol) was added and stirring continued at −10° C. for 3 hours. Ampicillin (0.35 g, 1 mmol) was added and the slurry stirred for 2 hours. The suspension was poured dropwise into ether (250 ml) and the solid was allowed to settle. The ether was decanted off. The solid was washed with a further portion of ether and then partitioned between aqueous NaHCO₃(pH 7.5)/ethylacetate. On acidification of the aqueous layer to pH 1.3, the precipitated product was filtered off (30 mg) and converted to the disodium salt as in Example 22.

δ (D⁶Acetone+D₂O) (free acid) 1.50, 1.60 (6H, 2s, gemdimethyls), 4.33 (1H, s, C-3 proton), 5.35 (2H, s, benzyl CH₂), 5.4–5.95 (3H, m, C-5 and C-6, β-lactam protons and C-α-proton), 7.2–7.7 (10H, m, aromatic protons), 8.68 (1H, s, C-6 pyrimidine proton).

Biological Data

TABLE 1

The antibacterial activities of a number of compounds of the present invention (MIC μg/ml)

| Organism | Compound of Example No. | | |
|---|---|---|---|
| | 1 | 2 | 16 |
| E coli ESS | <0.02 | <0.01 | 0.02 |
| E coli JT4 | >100 | >500 | >500 |
| E coli JT425 | 25 | 50 | 50 |
| E coli NCTC 10418 | 2.5 | 2.5 | 1.5 |
| Ps aeruginosa 10662 | 5.0 | 5.0 | 5 |
| Ps aeruginosa 10662 10⁻² | 2.5 | 2.5 | — |
| Ps aeruginosa Dalgleish 10⁻² | 50 | 125 | 125 |
| Serratia marcescens US32 | 10 | 12.5 | 12.5 |
| Klebsiella aerogenes A | 50 | 12.5 | 12.5 |
| Enterobacter cloacae N1 | 10 | 12.5 | 5 |
| P mirabilis C977 | 2.5 | 2.5 | 2.5 |
| P mirabilis 889 | >100 | >500 | >500 |
| P morganii | 50 | 25 | 5 |
| P rettgeri | 10 | 12.5 | 5 |
| B subtilis | 2.5 | 1.25 | 1.2 |
| Staph aureus Oxford | 0.5 | 1.25 | 1.2 |
| Staph aureus Russell | 50 | 125 | 125 |
| N catarrhalis 1502 | <0.02 | <0.01 | 0.02 |
| Step faecalis I | 5.0 | 5.0 | 5 |
| β-Haemolytic Strep CN10 | <0.02 | <0.01 | 0.02 |

TABLE 2

MIC values (μg/ml) of the compounds of the present invention against a gram negative organism (*E. coli* NCTC 10418) and a gram positive organism (*Staph. aureus* Oxford).

| Compound of Example No. | MIC (μg/ml) | |
|---|---|---|
| | E. coli NCTC 10418 | Staph. aureus Oxford |
| 1 | 2.5 | 0.5 |
| 2 | 2.5 | 1.25 |
| 3 | 5.0 | 1.2 |

TABLE 2-continued

MIC values (μg/ml) of the compounds of the present invention against a gram negative organism (*E. coli* NCTC 10418) and a gram positive organism (*Staph. aureus* Oxford).

| Compound of Example No. | MIC (μg/ml) | |
|---|---|---|
| | E. coli NCTC 10418 | Staph. aureus Oxford |
| 4 | 5 | 1.25 |
| 5 | 5.0 | 1.2 |
| 6 | 5.0 | 0.2 |
| 7 | 10 | 2.5 |
| 8 | 10 | 1.2 |
| 9 | 5.0 | 0.25 |
| 10 | 5.0 | 1.2 |
| 11 | 25 | 2.5 |
| 12 | 5.0 | 1.2 |
| 13 | 5.0 | 0.5 |
| 14 | 2.5 | 1.2 |
| 15 | 2.5 | 0.5 |
| 16 | 1.2 | 1.2 |
| 17 | 5.0 | 2.5 |
| 18 | 1.25 | 1.25 |
| 19 | 1.2 | 0.5 |
| 20 | 10 | 2.5 |
| 21 | 5.0 | 0.2 |
| 22 | 5.0 | 0.5 |
| 23 | 5.0 | 0.5 |
| 24 | 5.0 | 0.5 |
| 25 | 2.5 | 0.2 |

We claim:

1. A compound of the formula (I):

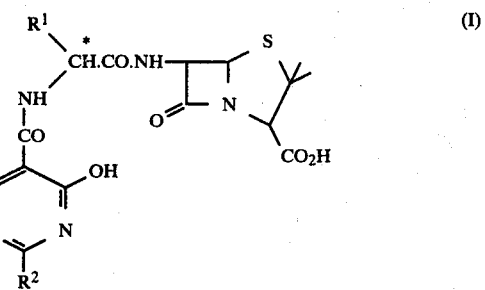

a pharmaceutically acceptable salt thereof or an in-vivo hydrolyzable ester thereof, wherein $R^1$ is phenyl, 4-hydroxyphenyl, 3,4-dihydroxyphenyl, 3,4-diacetoxyphenyl or a 5- or 6-membered heterocyclic ring containing up to three heteroatoms selected from the group consisting of oxygen, sulphur and nitrogen, said ring being unsubstituted or substituted by hydroxy, amino, halo, or alkoxy of 1 to 6 carbon atoms; and $R^2$ is a subgroup of the formula (A):

—NH—R³        (A)

wherein $R^3$ is alkyl of 1 to 10 carbon atoms unsubstituted or substituted by up to 3 substituents selected from the group consisting of halo, carboxy, alkoxycarbonyl of 1 to 6 carbon atoms in the alkoxy moiety, carbamoyl, phenyl or naphthyl unsubstituted or substituted by up to 5 substituents selected from the group consisting of halo, alkyl of 1 to 6 carbon atoms, alkoxy of 1 to 6 carbon atoms, haloalkyl of 1 to 6 carbon atoms, hydroxy, amino, sulphonamido, carboxy, alkoxycarbonyl of 1 to 6 carbon atoms in the alkoxy moiety and alkoxycarbonylalkyl of 1 to 6 carbon atoms in the alkoxy moiety and the alkyl moiety; or cycloalkyl of 3 to 7 carbon atoms; or (B):

—NH—CO—R⁴ (B)

wherein R⁴ is phenyl or naphthyl unsubstituted or substituted by up to 5 substituents selected from the group consisting of halo, alkyl of 1 to 6 carbon atoms, alkoxy of 1 to 6 carbon atoms, haloalkyl of 1 to 6 carbon atoms, hydroxy, amino, sulphonamido, carboxy, alkoxycarbonyl of 1 to 6 carbon atoms in the alkoxy moiety and alkoxycarbonylalkyl of 1 to 6 carbon atoms in the alkoxy moiety and the alkyl moiety; alkyl of 1 to 10 carbon atoms unsubstituted or substituted by up to 3 substituents selected from the group consisting of halo, carboxy, alkoxycarbonyl of 1 to 6 carbon atoms in the alkoxy moiety, carbamoyl, phenyl or naphthyl unsubstituted or substituted by up to 5 substituents selected from the group consisting of halo, alkyl of 1 to 6 carbon atoms, alkoxy of 1 to 6 carbon atoms, haloalkyl of 1 to 6 carbon atoms, hydroxy, amino, sulphonamido, carboxy, alkoxycarbonyl of 1 to 6 carbon atoms in the alkoxy moiety and alkoxycarbonylalkyl of 1 to 6 carbon atoms in the alkoxy moiety and the alkyl moiety; or alkyloxy of 1 to 6 carbon atoms unsubstituted or substituted by phenyl or naphthyl unsubstituted or substituted by up to 5 substituents selected from the group consisting of halo, alkyl of 1 to 6 carbon atoms, alkoxy of 1 to 6 carbon atoms, haloalkyl of 1 to 6 carbon atoms, hydroxy, amino, sulphonamido, carboxy, alkoxycarbonyl of 1 to 6 carbon atoms in the alkoxy moiety and alkoxycarbonylalkyl of 1 to 6 carbon atoms in the alkoxy moiety and the alkyl moiety.

2. A compound according to claim 1 wherein the carbon atom marked * in formula (I) is in the D-configuration.

3. A compound according to claim 1 or 2 wherein group R¹ is phenyl, 4-hydroxyphenyl, 3,4-dihydroxyphenyl, 2-thienyl, 3-thienyl or 2-amino-4-thiazolyl.

4. A compound according to claim 1 wherein R³ is alkyl of 3 to 8 carbon atoms.

5. A compound according to claim 1 wherein R² is phenylmethylamino, phenylethylamino, phenylpropylamino, 4-aminosulphonylphenylmethylamino, 4-methoxyphenylmethylamino, n-butylamino, n-hexylamino, 3-methoxypropyl-1-amino, ethylthioethylamino, butanoamido or benzoylamido.

6. A compound according to claim 1 wherein R³ and R⁴ are each alkyl of 1 to 6 carbon atoms unsubstituted or substituted by up to 3 substituents selected from the group consisting of halo, carboxy, alkoxycarbonyl of 1 to 6 carbon atoms in the alkoxy moiety, carbamoyl, phenyl or naphthyl unsubstituted or substituted by up to 5 substituents selected from the group consisting of halo, alkyl of 1 to 6 carbon atoms, alkoxy of 1 to 6 carbon atoms, haloalkyl of 1 to 6 carbon atoms, hydroxy, amino, sulphonamido, carboxy, alkoxycarbonyl of 1 to 6 carbon atoms in the alkoxy moiety and alkoxycarbonylalkyl of 1 to 6 carbon atoms in the alkoxy moiety and the alkyl moiety, heterocyclyl containing up to 4 heteroatoms selected from the group consisting of oxygen, nitrogen and sulphur unsubstituted or substituted with up to 3 moieties selected from the group consisting of halo, alkyl of 1 to 6 carbon atoms, alkoxy of 1 to 6 carbon atoms, haloalkyl of 1 to 6 carbon atoms, hydroxy, amino, carboxy, alkoxycarbonyl of 1 to 6 carbon atoms, alkoxycarbonylalkyl of 1 to 6 carbon atoms in the alkoxy moiety and the alkyl moiety, phenyl or naphthyl unsubstituted or substituted by up to 5 substituents selected from the group consisting of halo, alkyl of 1 to 6 carbon atoms, hydroxy, amino, sulphonamido, carboxy, alkoxycarbonyl of 1 to 6 carbon atoms in the alkoxy moiety and alkoxycarbonylalkyl of 1 to 6 carbon atoms in the alkoxy moiety and the alkyl moiety, or oxo, hydroxy, alkanoyloxy of 1 to 6 carbon atoms in the alkyl moiety, amino, mono- or di-alkylamino of 1 to 6 carbon atoms in each alkyl moiety, amino, alkylthio of 1 to 6 carbon atoms in the alkyl moiety, alkyloxy of 1 to 6 carbon atoms in the alkyl moiety, cycloalkyl of 3 to 7 carbon atoms and vinyl.

7. The compound according to claim 1 which is 6β-[D-2-(2-benzylamino-4-hydroxypyrimidine-5-carbonylamino)-2-phenyl] acetamido penicillanic acid.

8. The compound according to claim 1 which is 6β-[D-2-(2-(3-methoxypropyl-1-amino]-4-hydroxypyrimidine-5-carbonylamino)-2-phenyl] acetamido penicillanic acid.

9. The compound according to claim 1 which is 6β-[D-2-(2-3-phenylpropyl-1-amino)-4-hydroxypyrimidine-5-carbonylamino)-2-phenyl] acetamido penicillanic acid.

10. The compound according to claim 1 which is 6β-[D 2-(2-(2-phenylethyl-1-amino)-4-hydroxypyrmidine-5-carbonylamino)-2-(4-hydroxyphenyl)] acetamido penicillanic acid.

11. The compound according to claim 1 which is 6β-[D-2-(2-n-butylamino-4-hydroxypyrimidine-5-carbonylamino)-2-phenyl] acetamido penicillanic acid.

12. The compound according to claim 1 which is 6β-[D-2-(2-(n-hexylamino-4-hydroxypyrimidine-5-carbonylamino)-2-phenyl] acetamido penicillanic acid.

13. The compound according to claim 1 which is 6β-[D-2-(2-(2-ethylthioethyl-1-amino]-4-hydroxypyrimidine-5-carbonylamino)-2-phenyl] acetamido penicillanic acid.

14. A pharmaceutical composition useful for treating bacterial infections in humans and animals which comprises an antibacterially effective amount of a compound of the formula (I)

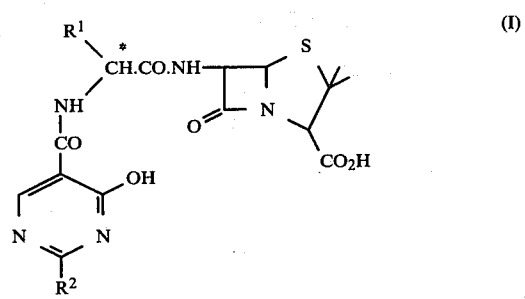

a pharmaceutically acceptable salt thereof or a pharmaceutically acceptable in-vivo hydrolyzable ester thereof, wherein R¹ is phenyl, 4-hydroxyphenyl, 3,4-dihydroxyphenyl, 3,4-diacetoxyphenyl or a 5- or 6-membered heterocyclic ring containing up to three heteroatoms selected from the group consisting of oxygen, sulphur and nitrogen, said ring being unsubstituted or substituted by hydroxy, amino, halo, or alkoxy of 1 to 6 carbon atoms; and R² is a sub-group of the formula (A):

—NH—R³ (A)

wherein R³ is alkyl of 1 to 10 carbon atoms unsubstituted or substituted by up to 3 substituents selected from the group consisting of halo, carboxy, alkoxycarbonyl of 1 to 6 carbon atoms in the alkoxy moiety, carbamoyl, phenyl or naphthyl unsubstituted or substituted by up to 5 substituents selected from the group consisting of halo, alkyl of 1 to 6 carbon atoms, alkoxy of 1 to 6 carbon atoms, haloalkyl of 1 to 6 carbon atoms, hydroxy, amino, sulphonamido, carboxy, alkoxycarbonyl of 1 to 6 carbon atoms in the alkoxy moiety and alkoxycarbonylalkyl of 1 to 6 carbon atoms in the alkoxy moiety and the alkyl moiety; or cycloalkyl of 3 to 7 carbon atoms; or (B):

$$-NH-CO-R^4 \qquad (B)$$

wherein $R^4$ is phenyl or naphthyl unsubstituted or substituted by up to 5 substituents selected from the group consisting of halo, alkyl of 1 to 6 carbon atoms, alkoxy of 1 to 6 carbon atoms, haloalkyl of 1 to 6 carbon atoms, hydroxy, amino, sulphonamido, carboxy, alkoxycarbonyl of 1 to 6 carbon atoms in the alkoxy moiety and alkoxycarbonylalkyl of 1 to 6 carbon atoms in the alkoxy moiety and the alkyl moiety; alkyl of 1 to 10 carbon atoms unsubstituted or substituted by up to 3 substituents selected from the group consisting of halo, carboxy, alkoxycarbonyl of 1 to 6 carbon atoms in the alkoxy moiety, carbamoyl, phenyl or naphthyl unsubstituted or substituted by up to 5 substituents selected from the group consisting of halo, alkyl of 1 to 6 carbon atoms, alkoxy of 1 to 6 carbon atoms, haloalkyl of 1 to 6 carbon atoms, hydroxy, amino, sulphonamido, carboxy, alkoxycarbonyl of 1 to 6 carbon atoms in the alkoxy moiety and alkoxycarbonylalkyl of 1 to 6 carbon atoms in the alkoxy moiety and the alkyl moiety; or alkyloxy of 1 to 6 carbon atoms unsubstituted or substituted by phenyl or naphthyl unsubstituted or substituted by up to 5 substituents selected from the group consisting of halo, alkyl of 1 to 6 carbon atoms, alkoxy of 1 to 6 carbon atoms, haloalkyl of 1 to 6 carbon atoms, hydroxy, amino, sulphonamido, carboxy, alkoxycarbonyl of 1 to 6 carbon atoms in the alkoxy moiety and alkoxycarbonylalkyl of 1 to 6 carbon atoms in the alkoxy moiety and the alkyl moiety, in combination with a pharmaceutically acceptable carrier.

15. A method of treating bacterial infections in humans and animals which comprises administering to a human or animal in need thereof, an antibacterially effective amount of a compound of the formula (I):

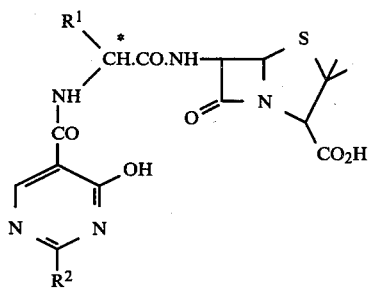

a pharmaceutically acceptable salt thereof or a pharmaceutically acceptable in-vivo hydrolyzable ester thereof, wherein $R^1$ is phenyl, 4-hydroxyphenyl, 3,4-dihydroxyphenyl, 3,4-diacetoxyphenyl or a 5- or 6-membered heterocyclic ring containing up to three heteroatoms selected heterocyclic ring containing up to three heteroatoms selected from the group consisting of oxygen, sulphur and nitrogen, said ring being unsubstituted or substituted by hydroxy, amino, halo, or alkoxy of 1 to 6 carbon atoms; and $R^2$ is a sub-group of the formula (A):

$$-NH-R^3 \qquad (A)$$

wherein $R^3$ is alkyl of 1 to 10 carbon atoms unsubstituted or substituted by up to 3 substituents selected from the group consisting of halo, carboxy, alkoxycarbonyl of 1 to 6 carbon atoms in the alkoxy moiety, carbamoyl, phenyl or naphthyl unsubstituted or substituted by up to 5 substituents selected from the group consisting of halo, alkyl of 1 to 6 carbon atoms, alkoxy of 1 to 6 carbon atoms, haloalkyl of 1 to 6 carbon atoms, hydroxy, amino, sulphonamido, carboxy, alkoxycarbonyl of 1 to 6 carbon atoms in the alkoxy moiety and alkoxycarbonylalkyl of 1 to 6 carbon atoms in the alkoxy moiety and the alkyl moiety; or cycloalkyl of 3 to 7 carbon atoms; or (B):

$$-NH-CO-R^4 \qquad (B)$$

wherein $R^4$ is phenyl or naphthyl unsubstituted or substituted by up to 5 substituents selected from the group consisting of halo, alkyl of 1 to 6 carbon atoms, alkoxy of 1 to 6 carbon atoms, haloalkyl of 1 to 6 carbon atoms, hydroxy, amino, sulphonamido, carboxy, alkoxycarbonyl of 1 to 6 carbon atoms in the alkoxy moiety and alkoxycarbonylalkyl of 1 to 6 carbon atoms in the alkoxy moiety and the alkyl moiety; alkyl of 1 to 10 carbon atoms unsubstituted or substituted by up to 3 substituents selected from the group consisting of halo, carboxy, alkoxycarbonyl of 1 to 6 carbon atoms in the alkoxy moiety, carbamoyl, phenyl or naphthyl unsubstituted or substituted by up to 5 substituents selected from the group consisting of halo, alkyl of 1 to 6 carbon atoms, alkoxy of 1 to 6 carbon atoms, haloalkyl of 1 to 6 carbon atoms, hydroxy, amino, sulphonamido, carboxy, alkoxycarbonyl of 1 to 6 carbon atoms in the alkoxy moiety and alkoxycarbonylalkyl of 1 to 6 carbon atoms in the alkoxy moiety and the alkyl moiety; or alkyloxy of 1 to 6 carbon atoms unsubstituted or substituted by phenyl or naphthyl unsubstituted or substituted by up to 5 substituents selected from the group consisting of halo, alkyl of 1 to 6 carbon atoms, alkoxy of 1 to 6 carbon atoms, haloalkyl of 1 to 6 carbon atoms, hydroxy, amino, sulphonamido, carboxy, alkoxycarbonyl of 1 to 6 carbon atoms in the alkoxy moiety and alkoxycarbonylalkyl of 1 to 6 carbon atoms in the alkoxy moiety and the alkyl moiety, in combination with a pharmaceutically acceptable carrier.

16. A pharmaceutical composition useful for treating bacterial infections in humans and animals which comprises an antibacterially effective amount of a compound of the formula (I):

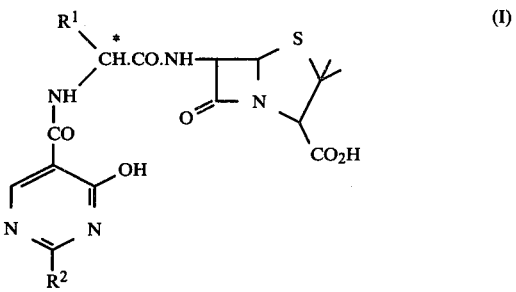

a pharmaceutically acceptable salt thereof or a pharmaceutically acceptable in-vivo hydrolyzable ester thereof, wherein $R^1$ is phenyl, 4-hydroxyphenyl, 3,4-dihydroxyphenyl, 3,4-diacetoxyphenyl or a 5- or 6-membered heterocyclic ring containing up to three heteroatoms selected heterocyclic ring containing up to three heteroatoms selected from the group consisting of oxygen, sulphur and nitrogen, said ring being unsubstituted or substituted by hydroxy, amino, halo, or alkoxy of 1 to 6 carbon atoms; and $R^2$ is a sub-group of the formula (A):

$$-NH-R^3 \qquad (A)$$

wherein $R^3$ is alkyl of 1 to 10 carbon atoms unsubstituted or substituted by up to 3 substituents selected from the group consisting of halo, carboxy, alkoxycarbonyl of 1 to 6 carbon atoms in the alkoxy moiety, carbamoyl, phenyl or naphthyl unsubstituted or substituted by up to 5 substituents selected from the group consisting of halo, alkyl of 1 to 6 carbon atoms, alkoxy of 1 to 6 carbon atoms, haloalkyl of 1 to 6 carbon atoms, hydroxy, amino, sulphonamido, carboxy, alkoxycarbonyl of 1 to 6 carbon atoms in the alkoxy moiety and alkoxycarbonylalkyl of 1 to 6 carbon atoms in the alkoxy moiety and the alkyl moiety; or cycloalkyl of 3 to 7 carbon atoms; or (B):

$$-NH-CO-R^4 \qquad (B)$$

wherein $R^4$ is phenyl or naphthyl unsubstituted or substituted by up to 5 substituents selected from the group consisting of halo, alkyl of 1 to 6 carbon atoms, alkoxy of 1 to 6 carbon atoms, haloalkyl of 1 to 6 carbon atoms, hydroxy, amino, sulphonamido, carboxy, alkoxycarbonyl of 1 to 6 carbon atoms in the alkoxy moiety and alkoxycarbonylalkyl of 1 to 6 carbon atoms in the alkoxy moiety and the alkyl moiety; alkyl of 1 to 10 carbon atoms unsubstituted or substituted by up to 3 substituents selected from the group consisting of halo, carboxy, alkoxycarbonyl of 1 to 6 carbon atoms in the alkoxy moiety, carbamoyl, phenyl or naphthyl unsubstituted or substituted by up to 5 substituents selected from the group consisting of halo, alkyl of 1 to 6 carbon atoms, alkoxy of 1 to 6 carbon atoms, haloalkyl of 1 to 6 carbon atoms, hydroxy, amino, sulphonamido, carboxy, alkoxycarbonyl of 1 to 6 carbon atoms in the alkoxy moiety and alkoxycarbonylalkyl of 1 to 6 carbon atoms in the alkoxy moiety and the alkyl moiety; or alkyloxy of 1 to 6 carbon atoms unsubstituted or substituted by phenyl or naphthyl unsubstituted or substituted by up to 5 substituents selected from the group consisting of halo, alkyl of 1 to 6 carbon atoms, alkoxy of 1 to 6 carbon atoms, haloalkyl of 1 to 6 carbon atoms, hydroxy, amino, sulphonamido, carboxy, alkoxycarbonyl of 1 to 6 carbon atoms in the alkoxy moiety and alkoxycarbonylalkyl of 1 to 6 carbon atoms in the alkoxy moiety and the alkyl moiety and a β-lactamase inhibitory amount of a β-lactamase inhibitor compatible with said compound, in combination with a pharmaceutically acceptable carrier.

17. A method of treating bacterial infections in humans and animals which comprises administering to a human or animal in need thereof, an antibacterially effective amount of a compound of the formula (I):

a pharmaceutically acceptable salt thereof or a pharmaceutically acceptable in-vivo hydrolyzable ester thereof, wherein $R^1$ is phenyl, 4-hydroxyphenyl, 3,4-dihydroxyphenyl, 3,4-diacetoxyphenyl or a 5- or 6-membered heterocyclic ring containing up to three heteroatoms selected heterocyclic ring containing up to three heteroatoms selected from the group consisting of oxygen, sulphur and nitrogen, said ring being unsubstituted or substituted by hydroxy, amino, halo, or alkoxy of 1 to 6 carbon atoms; and $R^2$ is a sub-group of the formula (A):

$$-NH-R^3 \qquad (A)$$

wherein $R^3$ is alkyl of 1 to 10 carbon atoms unsubstituted or substituted by up to 3 substituents selected from the group consisting of halo, carboxy, alkoxycarbonyl of 1 to 6 carbon atoms in the alkoxy moiety, carbamoyl, phenyl or naphthyl unsubstituted or substituted by up to 5 substituents selected from the group consisting of halo, alkyl of 1 to 6 carbon atoms, alkoxy of 1 to 6 carbon atoms, haloalkyl of 1 to 6 carbon atoms, hydroxy, amino, sulphonamido, carboxy, alkoxycarbonyl of 1 to 6 carbon atoms in the alkoxy moiety and alkoxycarbonylalkyl of 1 to 6 carbon atoms in the alkoxy moiety and the alkyl moiety; or cycloalkyl of 3 to 7 carbon atoms; or (B):

$$-NH-CO-R^4 \qquad (B)$$

wherein $R^4$ is phenyl or naphthyl unsubstituted or substituted by up to 5 substituents selected from the group consisting of halo, alkyl of 1 to 6 carbon atoms, alkoxy of 1 to 6 carbon atoms, haloalkyl of 1 to 6 carbon atoms, hydroxy, amino, sulphonamido, carboxy, alkoxycarbonyl of 1 to 6 carbon atoms in the alkoxy moiety and alkoxycarbonylalkyl of 1 to 6 carbon atoms in the alkoxy moiety and the alkyl moiety; alkyl of 1 to 10 carbon atoms unsubstituted or substituted by up to 3 substituents selected from the group consisting of halo, carboxy, alkoxycarbonyl of 1 to 6 carbon atoms in the alkoxy moiety, carbamoyl, phenyl or naphthyl unsubstituted or substituted by up to 5 substituents selected from the group consisting of halo, alkyl of 1 to 6 carbon atoms, alkoxy of 1 to 6 carbon atoms, haloalkyl of 1 to 6 carbon atoms, hydroxy, amino, sulphonamido, carboxy, alkoxycarbonyl of 1 to 6 carbon atoms in the alkoxy moiety and alkoxycarbonylalkyl of 1 to 6 carbon atoms in the alkoxy moiety and the alkyl moiety and a δ-lactamase inhibitory amount of a β-lactamase inhibitor compatible with said compound, in combination with a pharmaceutically acceptable carrier.

18. A pharmaceutical composition useful for treating bacterial infections in humans and animals which comprises an antibacterially effective amount of a compound of the formula (I):

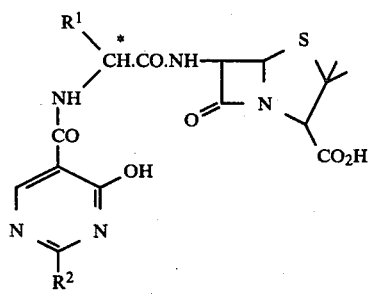

a pharmaceutically acceptable salt thereof or a pharmaceutically acceptable in-vivo hydrolyzable ester thereof, wherein $R^1$ is phenyl, 4-hydroxyphenyl, 3,4-dihydroxyphenyl, 3,4-diacetoxyphenyl or a 5- or 6-membered heterocyclic ring containing up to three heteroatoms selected heterocyclic ring containing up to three heteroatoms selected from the group consisting of oxygen, sulphur and nitrogen, said ring being unsubstituted or substituted by hydroxy, amino, halo, or alkoxy of 1 to 6 carbon atoms; and $R^2$ is a sub-group of the formula (A):

 (A)

wherein $R^3$ is alkyl of 1 to 10 carbon atoms unsubstituted or substituted by up to 3 substituents selected from the group consisting of halo, carboxy, alkoxycarbonyl of 1 to 6 carbon atoms in the alkoxy moiety, carbamoyl, phenyl or naphthyl unsubstituted or substituted by up to 5 substituents selected from the group consisting of halo, alkyl of 1 to 6 carbon atoms, alkoxy of 1 to 6 carbon atoms, haloalkyl of 1 to 6 carbon atoms, hydroxy, amino, sulphonamido, carboxy, alkoxycarbonyl of 1 to 6 carbon atoms in the alkoxy moiety and alkoxycarbonylalkyl of 1 to 6 carbon atoms in the alkoxy moiety and the alkyl moiety; or cycloalkyl of 3 to 7 carbon atoms; or (B):

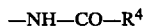 (B)

wherein $R^4$ is phenyl or naphthyl unsubstituted or substituted by up to 5 substituents selected from the group consisting of halo, alkyl of 1 to 6 carbon atoms, alkoxy of 1 to 6 carbon atoms, haloalkyl of 1 to 6 carbon atoms, hydroxy, amino, sulphonamido, carboxy, alkoxycarbonyl of 1 to 6 carbon atoms in the alkoxy moiety and alkoxycarbonylalkyl of 1 to 6 carbon atoms in the alkoxy moiety and the alkyl moiety; alkyl of 1 to 10 carbon atoms unsubstituted or substituted by up to 3 substituents selected from the group consisting of halo, carboxy, alkoxycarbonyl of 1 to 6 carbon atoms in the alkoxy moiety, carbamoyl, phenyl or naphthyl unsubstituted or substituted by up to 5 substituents selected from the group consisting of halo, alkyl of 1 to 6 carbon atoms, alkoxy of 1 to 6 carbon atoms, haloalkyl of 1 to 6 carbon atoms, hydroxy, amino, sulphonamido, carboxy, alkoxycarbonyl of 1 to 6 carbon atoms in the alkoxy moiety and alkoxycarbonylalkyl of 1 to 6 carbon atoms, in the alkoxy moiety and the alkyl moiety; or alkyloxy of 1 to 6 carbon atoms unsubstituted or substituted by phenyl or naphthyl unsubstituted or substituted by up to 5 substituents selected from the group consisting of halo, alkyl of 1 to 6 carbon atoms, alkoxy of 1 to 6 carbon atoms, haloalkyl of 1 to 6 carbon atoms, hydroxy, amino, sulphonamido, carboxy, alkoxycarbonyl of 1 to 6 carbon atoms in the alkoxy moiety and alkoxycarbonylalkyl of 1 to 6 carbon atoms in the alkoxy moiety and the alkyl moiety and a thereapeutically effective amount of a compound of the formula (VIII):

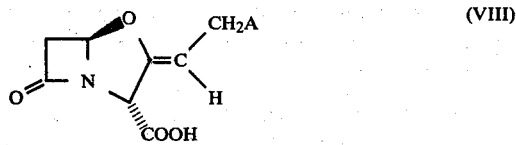

or a pharmaceutically acceptable salt or pharmaceutically acceptable ester thereof, wherein A is hydroxyl, substituted hydroxyl, thio, substituted thio, amino, mono- or di-hydrocarbyl-substituted amino, or mono- or di-acylamino, in combination with a pharmaceutically acceptable carrier.

19. A method of treating bacterial infections in humans and animals which comprises administering to a human or animal in need thereof, an antibacterially effective amount of a compound of the formula (I):

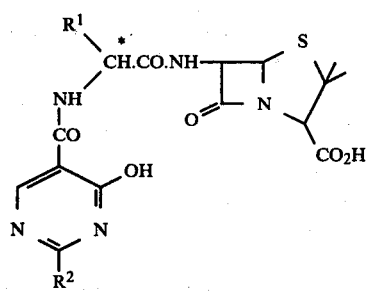

a pharmaceutically acceptable salt thereof or a pharmaceutically acceptable in-vivo hydrolyzable ester thereof, wherein $R^1$ is phenyl, 4-hydroxyphenyl, 3,4-dihydroxyphenyl, 3,4-diacetoxyphenyl or a 5- or 6-membered heterocyclic ring containing up to three heteroatoms selected heterocyclic ring containing up to three heteroatoms selected from the group consisting of oxygen, sulphur and nitrogen, said ring being unsubstituted or substituted by hydroxy, amino, halo, or alkoxy of 1 to 6 carbon atoms; and $R^2$ is a sub-group of the formula (A):

 (A)

wherein $R^3$ is alkyl of 1 to 10 carbon atoms unsubstituted or substituted by up to 3 substituents selected from the group consisting of halo, carboxy, alkoxycarbonyl of 1 to 6 carbon atoms in the alkoxy moiety, carbamoyl, phenyl or naphthyl unsubstituted or substituted by up to 5 substituents selected from the group consisting of halo, alkyl of 1 to 6 carbon atoms, alkoxy of 1 to 6 carbon atoms, haloalkyl of 1 to 6 carbon atoms, hydroxy, amino, sulphonamido, carboxy, alkoxycarbonyl of 1 to 6 carbon atoms in the alkoxy moiety and alkoxycarbonylalkyl of 1 to 6 carbon atoms in the alkoxy moiety and the alkyl moiety; or cycloalkyl of 3 to 7 carbon atoms; or (B):

—NH—CO—R$^4$            (B)

wherein R$^4$ is phenyl or naphthyl unsubstituted or substituted by up to 5 substituents selected from the group consisting of halo, alkyl of 1 to 6 carbon atoms, alkoxy of 1 to 6 carbon atoms, haloalkyl of 1 to 6 carbon atoms, hydroxy, amino, sulphonamido, carboxy, alkoxycarbonyl of 1 to 6 carbon atoms in the alkoxy moiety and alkoxycarbonylalkyl of 1 to 6 carbon atoms in the alkoxy moiety and the alkyl moiety; alkyl of 1 to 10 carbon atoms unsubstituted or substituted by up to 3 substituents selected from the group consisting of halo, carboxy, alkoxycarbonyl of 1 to 6 carbon atoms in the alkoxy moiety, carbamoyl, phenyl or naphthyl unsubstituted or substituted by up to 5 substituents selected from the group consisting of halo, alkyl of 1 to 6 carbon atoms, alkoxy of 1 to 6 carbon atoms, haloalkyl of 1 to 6 carbon atoms, hydroxy, amino, sulphonamido, carboxy, alkoxycarbonyl of 1 to 6 carbon atoms in the alkoxy moiety and alkoxycarbonylalkyl of 1 to 6 carbon atoms in the alkoxy moiety and the alkyl moiety; or alkyloxy of 1 to 6 carbon atoms unsubstituted or substituted by phenyl or naphthyl unsubstituted or substituted by up to 5 substituents selected from the group consisting of halo, alkyl of 1 to 6 carbon atoms, alkoxy of 1 to 6 carbon atoms, haloalkyl of 1 to 6 carbon atoms, hydroxy, amino, sulphonamido, carboxy, alkoxycarbonyl of 1 to 6 carbon atoms in the alkoxy moiety and alkoxycarbonylalkyl of 1 to 6 carbon atoms in the alkoxy moiety and the alkyl moiety and a therapeutically effective amount of a compound of the formula (VIII):

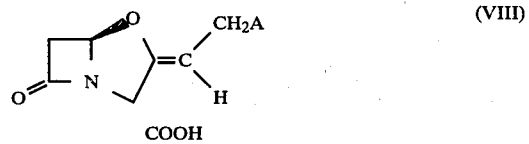

or a pharmaceutically acceptable salt or pharmaceutically acceptable ester thereof, wherein A is hydroxyl, substituted hydroxyl, thio, substituted thiol, amino, mono- or di-hydrocarbyl-substituted amino, or mono- or di-acylamino, in combination with a pharmaceutically acceptable carrier.

20. A pharmaceutical composition useful for treating bacterial infections in humans and animals which comprises an antibacterially effective amount of a compound of the formula (I):

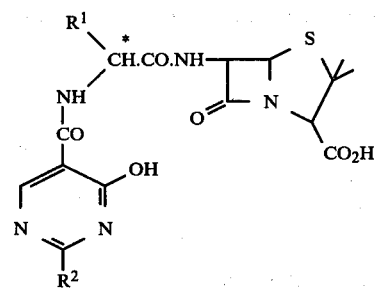

a pharmaceutically acceptable salt thereof or a pharmaceutically acceptable in-vivo hydrolyzable ester thereof, wherein R$^1$ is phenyl, 4-hydroxyphenyl, 3,4-dihydroxyphenyl, 3,4-diacetoxyphenyl or a 5- or 6-membered heterocyclic ring containing up to three heteroatoms selected heterocyclic ring containing up to three heteroatoms selected from the group consisting of oxygen, sulphur and nitrogen, said ring being unsubstituted or substituted by hydroxy, amino, halo, or alkoxy of 1 to 6 carbon atoms; and R$^2$ is a sub-group of the formula (A):

—NH—R$^3$            (A)

wherein R$^3$ is alkyl of 1 to 10 carbon atoms unsubstituted or substituted by up to 3 substituents selected from the group consisting of halo, carboxy, alkoxycarbonyl of 1 to 6 carbon atoms in the alkoxy moiety, carbamoyl, phenyl or naphthyl unsubstituted or substituted by up to 5 substituents selected from the group consisting of halo, alkyl of 1 to 6 carbon atoms, alkoxy of 1 to 6 carbon atoms, haloalkyl of 1 to 6 carbon atoms, hydroxy, amino, sulphonamido, carboxy, alkoxycarbonyl of 1 to 6 carbon atoms in the alkoxy moiety and alkoxycarbonylalkyl of 1 to 6 carbon atoms in the alkoxy moiety and the alkyl moiety; or cycloalkyl of 3 to 7 carbon atoms; or (B):

—NH—CO—R$^4$            (B)

wherein R$^4$ is phenyl or naphthyl unsubstituted or substituted by up to 5 substituents selected from the group consisting of halo, alkyl of 1 to 6 carbon atoms, alkoxy of 1 to 6 carbon atoms, haloalkyl of 1 to 6 carbon atoms, hydroxy, amino, sulphonamido, carboxy, alkoxycarbonyl of 1 to 6 carbon atoms in the alkoxy moiety and alkoxycarbonylalkyl of 1 to 6 carbon atoms in the alkoxy moiety and the alkyl moiety; alkyl of 1 to 10 carbon atoms unsubstituted or substituted by up to 3 substituents selected from the group consisting of halo, carboxy, alkoxycarbonyl of 1 to 6 carbon atoms in the alkoxy moiety, carbamoyl, phenyl or naphthyl unsubstituted or substituted by up to 5 substituents selected from the group consisting of halo, alkyl of 1 to 6 carbon atoms, alkoxy of 1 to 6 carbon atoms, haloalkyl of 1 to 6 carbon atoms, hydroxy, amino, sulphonamido, carboxy, alkoxycarbonyl of 1 to 6 carbon atoms in the alkoxy moiety and alkoxycarbonylalkyl of 1 to 6 carbon atoms in the alkoxy moiety and the alkyl moiety; or alkyloxy of 1 to 6 carbon atoms unsubstituted or substituted by phenyl or naphthyl unsubstituted or substituted by up to 5 substituents selected from the group consisting of halo, alkyl of 1 to 6 carbon atoms, alkoxy of 1 to 6 carbon atoms, haloalkyl of 1 to 6 carbon atoms, hydroxy, amino, sulphonamido, carboxy, alkoxycarbonyl of 1 to 6 carbon atoms in the alkoxy moiety and alkoxycarbonylalkyl of 1 to 6 carbon atoms in the alkoxy moiety and the alkyl moiety and a therapeutically effective amount of a compound of the formula (IX):

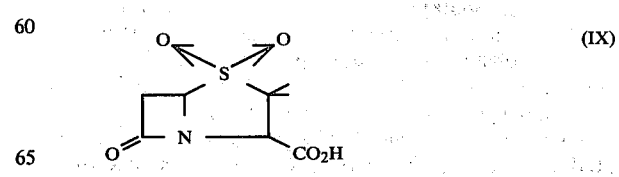

a pharmaceutically acceptable salt thereof or a pharmaceutically acceptable in-vivo hydrolyzable ester thereof, in combination with a pharmaceutically acceptable carrier.

21. A method of treating bacterial infections in humans and animals which comprises administering to a human or animal in need thereof, an antibacterially effective amount of a compound of the formula (I):

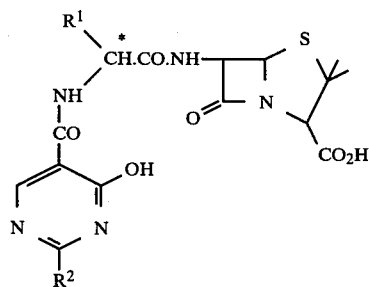

a pharmaceutically acceptable salt thereof or a pharmaceutically acceptable in-vivo hydrolyzable ester thereof, wherein R¹ is phenyl, 4-hydroxyphenyl, 3,4-dihydroxyphenyl, 3,4-diacetoxyphenyl or a 5- or 6-membered heterocyclic ring containing up to three heteroatoms selected heterocyclic ring containing up to three heteroatoms selected from the group consisting of oxygen, sulphur and nitrogen, said ring being unsubstituted or substituted by hydroxy, amino, halo, or alkoxy of 1 to 6 carbon atoms; and R² is a sub-group of the formula (A):

—NH—R³ (A)

wherein R³ is alkyl of 1 to 10 carbon atoms unsubstituted or substituted by up to 3 substituents selected from the group consisting of halo, carboxy, alkoxycarbonyl of 1 to 6 carbon atoms in the alkoxy moiety, carbamoyl, phenyl or naphthyl unsubstituted or substituted by up to 5 substituents selected from the group consisting of halo, alkyl of 1 to 6 carbon atoms, alkoxy of 1 to 6 carbon atoms, haloalkyl of 1 to 6 carbon atoms, hydroxy, amino, sulphonamido, carboxy, alkoxycarbonyl of 1 to 6 carbon atoms in the alkoxy moiety and alkoxycarbonylalkyl of 1 to 6 carbon atoms in the alkoxy moiety and the alkyl moiety; or cycloalkyl of 3 to 7 carbon atoms; or (B):

—NH—CO—R⁴ (B)

wherein R⁴ is phenyl or naphthyl unsubstituted or substituted by up to 5 substituents selected from the group consisting of halo, alkyl of 1 to 6 carbon atoms, alkoxy of 1 to 6 carbon atoms, haloalkyl of 1 to 6 carbon atoms, hydroxy, amino, sulphonamido, carboxy, alkoxycarbonyl of 1 to 6 carbon atoms in the alkoxy moiety and alkoxycarbonylalkyl of 1 to 6 carbon atoms in the alkoxy moiety and the alkyl moiety; alkyl of 1 to 10 carbon atoms unsubstituted or substituted by up to 3 substituents selected from the group consisting of halo, carboxy, alkoxycarbonyl of 1 to 6 carbon atoms in the alkoxy moiety, carbamoyl, phenyl or naphthyl unsubstituted or substituted by up to 5 substituents selected from the group consisting of halo, alkyl of 1 to 6 carbon atoms, alkoxy of 1 to 6 carbon atoms, haloalkyl of 1 to 6 carbon atoms, hydroxy, amino, sulphonamido, carboxy, alkoxycarbonyl of 1 to 6 carbon atoms in the alkoxy moiety and alkoxycarbonylalkyl of 1 to 6 carbon atoms in the alkoxy moiety and the alkyl moiety; or alkyloxy of 1 to 6 carbon atoms unsubstituted or substituted by phenyl or naphthyl unsubstituted or substituted by up to 5 substituents selected from the group consisting of halo, alkyl of 1 to 6 carbon atoms, alkoxy of 1 to 6 carbon atoms, haloalkyl of 1 to 6 carbon atoms, hydroxy, amino, sulphonamido, carboxy, alkoxycarbonyl of 1 to 6 carbon atoms in the alkoxy moiety and alkoxycarbonylalkyl of 1 to 6 carbon atoms in the alkoxy moiety and the alkyl moiety and a therapeutically effective amount of a compound of the formula (IX):

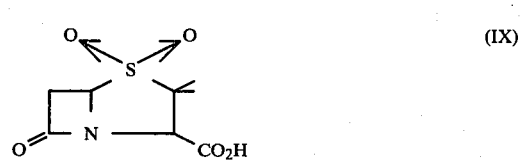

a pharmaceutically acceptable salt thereof or a pharmaceutically acceptable in-vivo hydrolyzable ester thereof, in combination with a pharmaceutically acceptable carrier.

* * * * *